United States Patent
Hu et al.

(10) Patent No.: US 10,781,206 B2
(45) Date of Patent: Sep. 22, 2020

(54) TETRAHYDROPYRAZOLOPYRIDINE COMPOUNDS FOR THE TREATMENT OF INFECTIOUS DISEASES

(71) Applicant: Hoffmann-La Roche Inc., Little Falls, NJ (US)

(72) Inventors: Taishan Hu, Shanghai (CN); Hong Shen, Shanghai (CN); Xingchun Han, Shanghai (CN)

(73) Assignee: HOFFMANN LA-ROCHE INC., Little Falls, NJ (US)

( * ) Notice: Subject to any disclaimer, the term of this patent is extended or adjusted under 35 U.S.C. 154(b) by 0 days.

(21) Appl. No.: 16/247,132

(22) Filed: Jan. 14, 2019

(65) Prior Publication Data
US 2019/0248786 A1    Aug. 15, 2019

Related U.S. Application Data

(63) Continuation of application No. PCT/EP2017/067188, filed on Jul. 10, 2017.

(51) Int. Cl.
C07D 471/04 (2006.01)
A61P 31/20 (2006.01)

(52) U.S. Cl.
CPC ............ *C07D 471/04* (2013.01); *A61P 31/20* (2018.01)

(58) Field of Classification Search
CPC .............................. C07D 471/04; A61K 31/437
See application file for complete search history.

(56) References Cited

U.S. PATENT DOCUMENTS

| | | | |
|---|---|---|---|
| 9,527,845 B2 * | 12/2016 | Hartman | C12N 7/00 |
| 2011/0262397 A1 * | 10/2011 | Slomczynska | C07D 487/04 424/85.4 |
| 2016/0185778 A1 * | 6/2016 | Hartman | C12N 7/00 424/85.7 |

FOREIGN PATENT DOCUMENTS

| | | |
|---|---|---|
| WO | 2009/085983 A1 | 7/2009 |
| WO | 2010/096115 A1 | 8/2010 |
| WO | 2013/096744 A1 | 6/2013 |
| WO | 2014/033167 A1 | 3/2014 |
| WO | 2014/033170 A1 | 3/2014 |
| WO | 2014/111871 A1 | 7/2014 |
| WO | 2014/152725 A1 | 9/2014 |
| WO | 2016/109689 A2 | 7/2016 |
| WO | 2016/109689 A3 | 7/2016 |
| WO | 2016/113273 A1 | 7/2016 |
| WO | 2017/198744 A1 | 11/2017 |

OTHER PUBLICATIONS

Blaszykowski, J Org Chem, vol. 73(5), 1888-1897, 2008. (Year: 2008).*
Deres et al., "Inhibition of Hepatitis B Virus Replication by Drug-Induced Depletion of Nucleocapsids" Science 299(5608):893-897 (Feb. 7, 2003).
Feld et al., "The phenylpropenamide derivative AT-130 blocks HBV replication at the level of viral RNA packaging" Antiviral Res 76:168-177 (2007).
International Search Report for PCT/EP2017/067188 dated Oct. 13, 2017.

\* cited by examiner

*Primary Examiner* — D Margaret M Seaman
(74) *Attorney, Agent, or Firm* — Richard G. A. Bone; Genentech, Inc.

(57) ABSTRACT

The present invention relates to compounds of the formula (I),

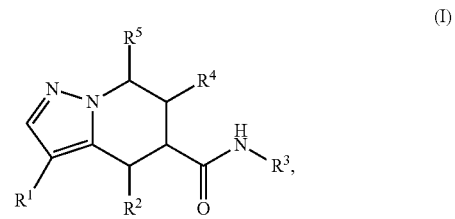

or pharmaceutically acceptable salts, enantiomer or diastereomer thereof, wherein $R^1$ to $R^5$ are as described above. The compounds may be useful for the treatment or prophylaxis of hepatitis B virus infection.

17 Claims, No Drawings

TETRAHYDROPYRAZOLOPYRIDINE COMPOUNDS FOR THE TREATMENT OF INFECTIOUS DISEASES

RELATED APPLICATIONS

This application is a continuation of International Application No. PCT/EP2017/067188, filed Jul. 10, 2017, which claims priority to Application No. PCT/CN2016/090041, filed Jul. 14, 2016, each of which is incorporated herein by reference in its entirety.

The present invention relates to organic compounds useful for therapy and/or prophylaxis in a mammal, and in particular for treating hepatitis B virus infection, and their pharmaceutical activity, manufacture, pharmaceutical compositions containing them and their potential use as medicaments.

FIELD OF THE INVENTION

The present invention relates to compounds of the formula (I),

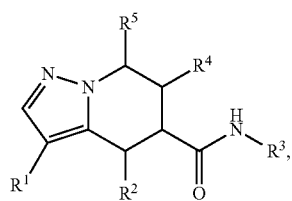

(I)

or pharmaceutically acceptable salts, enantiomer or diastereomer thereof, wherein $R^1$ to $R^5$ are as described below. The compounds of this invention are useful for the treatment or prophylaxis of hepatitis B virus infection.

Hepatitis B virus (HBV) infection is a major public health problem worldwide, roughly 30% of the world's population show serological evidence of current or past infection. Despite the introduction of a safe and effective prophylactic vaccine against the virus in the early 1980s, it is estimated that there are still more than 240 million chronic HBV carriers worldwide, a high percentage of whom will eventually develop liver cirrhosis or hepatocellular carcinoma (HCC) (WHO Hepatitis B. Fact Sheet N° 204). In the 2010 Global Burden of Disease study (R Lozano, et al. Lancet, 380 (2012), 2095-2128), HBV infection ranked in the top health priorities in the world, and was the tenth leading cause of death (780,000 deaths per year). Recent studies have shown that progression to liver cirrhosis and HCC in patients with chronic HBV infection is significantly associated with circulating HBV DNA levels. Thus, antiviral therapy against HBV is critical to prevent the progression to cirrhosis or development of HCC.

HBV is a small, enveloped virus that belongs to the Hepadnaviridae family. It contains a partly double-stranded DNA genome with approximately 3200 base pairs. HBV have a strong preference for infecting human hepatocytes. The life cycle begins when HBV attaches to the host cell membrane via its envelope proteins. The precise mechanism of viral entry has not been fully elucidated. The viral relaxed circular DNA (rcDNA) containing nucleocapsids are released into the cytoplasm and transported to the nucleus. In the nucleus, the rcDNA is repaired by both viral and cellular enzymes to form covalently closed circular DNA (cccDNA). There is evidence that each infected cell contains 1-50 cccDNA molecules as unique episomal minichromosomes. Both subgenomic RNA (sgRNA) and pregenomic RNA (pgRNA) are transcribed from the cccDNA using the cellular transcriptional machinery. After nuclear export, the pgRNA is translated into the core protein and the viral polymerase. The sgRNA is translated into the regulatory X protein and the three envelope proteins. Self-assembly of the RNA-containing viral nucleocapsid takes place via complex formation of the pgRNA with the core protein and the polymerase. Inside the nucleocapsid, the pgRNA is reverse transcribed into negative-strand DNA. rcDNA is then generated by plus-strand synthesis from the negative-strand DNA. The nucleocapsids are either re-imported to the nucleus for cccDNA amplification or enveloped and released via the endoplasmic reticulum (ER). The reverse transcriptase lacks proofreading activity; thus, mutations of the viral genome are frequent and result in the coexistence of genetically distinct viral species in infected individuals (quasispecies).

Currently, seven treatments are approved for chronic hepatitis B (CHB), including two formulations of interferon (IFN) (conventional IFN and PEG-IFN) and five nucleos(t) ide analogues (NUCs: lamivudine, adefovir dipivoxil, entecavir, telbivudine, and tenofovir disoproxil). The main difference between immunomodulatory agents and NUCs is that PEG-IFN has the advantage of a finite duration of use, whereas the use of NUCs is indefinite. The major drawback of PEG-IFN is its high frequency of adverse events. Some viral genotypes do not show good responses to interferon therapy. Long-term use of NUCs, on the other hand, poses the risk of drug resistance. The ultimate goal of antiviral therapy for CHB is to prevent progression to cirrhosis or HCC via eradication of HBV or persistent viral suppression. The majority of currently treated patients fail to achieve this goal. As indicated above, nucleocapsid assembly is a critical step for HBV genome replication. As the synthesis of viral DNA takes place exclusively within the nucleocapsid, the assembly and disassembly of nucleocapsid must be precisely regulated to ensure correct packaging and release of the viral genome. Nucleocapsid assembly is an evolutionary constraint process that limits the diversity of HBV, and it is highly sensitive to even subtle molecular disturbances. Both assembly and disassembly of nucleocapsid make the process an attractive therapeutic target for the development of new antiviral therapies against various HBV genotypes and drug resistance isolates. A few capsid related anti-HBV compounds have been reported. For example, heteroaryldihydropyrimidines (HAP), including compounds named Bay 41-4109, Bay 38-7690 and Bay 39-5493 (Deres K. et al. Science 2003, 893), and phenylpropenamide derivatives such as AT-61 and AT-130 (Feld J. et al. Antiviral Research 2007, 168-177). Capsid has become a promising drug target with several molecules under clinical stage. There is still a need to develop new treatments for the prophylaxis and treatment of hepatitis B virus infection.

SUMMARY OF THE INVENTION

The present invention relates to novel compounds of formula (I),

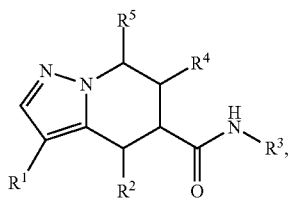

(I)

wherein
$R^1$ is $C_{3-7}$cycloalkyl;
  dioxothiadiazolidinyl, said dioxothiadiazolidinyl being unsubstituted or substituted by benzyl; dioxothiazolidinyl;
  oxomorpholinyl;
  oxooxazolidinyl, said oxooxazolidinyl being once or twice substituted by $C_{1-6}$alkyl;
  oxopyrrolidinyl, said oxooxazolidinyl being unsubstituted or substituted by cyano or $C_{1-6}$alkyloxadiazolyl;
  phenyl, said phenyl being once or twice substituted by halogen; or
  pyridinyl, said pyridinyl being once or twice substituted by halogen;
$R^2$ is H or $C_{1-6}$alkyl;
$R^3$ is phenyl, said phenyl being once, twice or three times substituted by substituents independently selected from cyano, halogen, $C_{1-6}$alkyl and halo$C_{1-6}$alkyl;
  pyridinyl, said pyridinyl being once or twice substituted by halogen; or
  thienyl;
$R^4$ is H or $C_{1-6}$alkyl;
$R^5$ is H or $C_{1-6}$alkyl;
or pharmaceutically acceptable salt, enantiomer or diastereomer thereof.

Objects of the present invention are novel compounds of formula (I), their manufacture, medicaments based on a compound in accordance with the invention and their production as well as the use of compounds of formula (I) as HBV inhibitors and for the treatment or prophylaxis of HBV infection.

DETAILED DESCRIPTION OF THE INVENTION

Definitions

The term "$C_{1-6}$alkyl" denotes a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include, but not limited to, methyl, ethyl, propyl, isopropyl, n-butyl, iso-butyl, sec-butyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_3$-7cycloalkyl" group is cyclopentyl.

The term "halo" or "halogen" are used interchangeably herein and denote fluoro, chloro, bromo or iodo.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, trifluoroethyl, fluoromethyl, difluoromethyl, difluoroethyl or trifluoromethyl.

The term "oxo" denotes a divalent oxygen atom =O.

The term "aryl" denotes a monovalent aromatic carbocyclic ring system comprising 6 to 10 carbon ring atoms. Example of aryl include, but not limited to, phenyl, cyanofluorophenyl, methylfluorophenyl, trifluorophenyl, trifluoromethylfluorophenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include, but not limited to, pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl or quinoxalinyl.

Heteroaryl can be further substituted by halogen, $C_{1-6}$alkyl, halo$C_{1-6}$alkyl, cyano, $C_{3-7}$cycloalkyl, $(C_{1-6}$alkyl$)_2$amino, $C_{1-6}$alkoxy. Example of heteroaryl include, but not limited to, chloropyridinyl, chlorothiazolyl, cyanopyrazolyl, cyanopyridinyl, fluorochloropyridinyl, fluoropyrazolyl, fluoropyridinyl, difluoropyridinyl, fluoropyrimidinyl, hydroxymethylpyrazolyl, methoxymethylpyrazolyl, methylfluoropyridinyl, methylfluoropyrimidinyl, methylpyrazolyl, trifluoromethylpyridinyl and trifluoromethylthiazolyl.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, and lactam including, but not limited to, dioxothiadiazolidinyl, dioxothiazolidinyl, oxopyrrolidinyl, oxomorpholinyl, oxooxazolidinyl and oxooxazinanyl; monocyclic saturated heterocyclyl can be further substituted by benzyl, cyano, $C_{1-6}$alkyl, halogen, halo$C_{1-6}$alkyl or $C_{1-6}$ alkyloxadiazolyl. Examples for substituted monocyclic saturated heterocyclyl include, but not limited to, dioxothiadiazolidinyl, benzyldioxothiadiazolidinyl, dioxothiadiazolidinyl, oxomorpholinyl, dimetyloxooxazolidinyl, oxopyrrolidinyl, cyanooxopyrrolidinyl and methyloxadiazolyloxopyrrolidinyl.

The term "diastereomer" denotes a stereoisomer with two or more centers of chirality and whose molecules are not mirror images of one another. Diastereomers have different physical properties, e.g. melting points, boiling points, spectral properties, activities and reactivities.

The term "enantiomers" denotes two stereoisomers of a compound which are non-superimposable mirror images of one another.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBV

The present invention provides (i) novel compounds having the general formula (I),

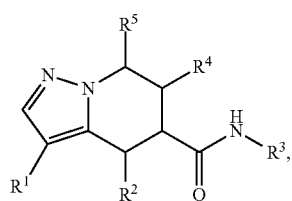

(I)

wherein
$R^1$ is $C_{3-7}$cycloalkyl;
  dioxothiadiazolidinyl, said dioxothiadiazolidinyl being unsubstituted or substituted by benzyl;
  dioxothiazolidinyl;
  oxomorpholinyl;
  oxooxazolidinyl, said oxooxazolidinyl being once or twice substituted by $C_{1-6}$alkyl; oxopyrrolidinyl, said oxooxazolidinyl being unsubstituted or substituted by cyano or $C_{1-6}$alkyloxadiazolyl;
  phenyl, said phenyl being once or twice substituted by halogen;
  pyridinyl, said pyridinyl being once or twice substituted by halogen;
$R^2$ is H or $C_{1-6}$alkyl;
$R^3$ is phenyl, said phenyl being once, twice or three times substituted by substituents independently selected from cyano, halogen, $C_{1-6}$alkyl and halo$C_{1-6}$alkyl;
  pyridinyl, said pyridinyl being once or twice substituted by halogen; or
  thienyl;
$R^4$ is H or $C_{1-6}$alkyl;
$R^5$ is H or $C_{1-6}$alkyl;
or pharmaceutically acceptable salt, enantiomer or diastereomer thereof.

Another embodiment of present invention is relates to (ii) a compound of formula (I), wherein
$R^1$ is $C_{3-7}$cycloalkyl;
  dioxothiadiazolidinyl, said dioxothiadiazolidinyl being unsubstituted or substituted by benzyl;
  dioxothiazolidinyl;
  oxomorpholinyl;
  oxooxazolidinyl, said oxooxazolidinyl being twice substituted by $C_{1-6}$alkyl;
  oxopyrrolidinyl, said oxooxazolidinyl being unsubstituted or substituted by cyano or $C_{1-6}$alkyloxadiazolyl;
  phenyl, said phenyl being twice substituted by halogen;
  pyridinyl substituted by halogen;
$R^2$ is H;
$R^3$ is phenyl, said phenyl being once, twice or three times substituted by substituents independently selected from cyano, halogen, $C_{1-6}$alkyl and halo$C_{1-6}$alkyl;
  pyridinyl, said pyridinyl being once or twice substituted by halogen; or
  thienyl;
$R^4$ is H;
$R^5$ is H;
or pharmaceutically acceptable salt, enantiomer or diastereomer thereof.

A further embodiment of present invention is (iii) a compound of formula (I), wherein
$R^1$ is cyclopentyl, dioxothiadiazolidinyl, benzyldioxothiadiazolidinyl, dioxothiazolidinyl, oxomorpholinyl, dimetyloxooxazolidinyl, oxopyrrolidinyl, cyanooxopyrrolidinyl, methyloxadiazolyloxopyrrolidinyl, difluorophenyl or fluoropyridinyl;
$R^2$ is H;
$R^3$ is cyanofluorophenyl, methylfluorophenyl, trifluorophenyl, trifluoromethylfluorophenyl, fluoropyridinyl, difluoropyridinyl or thienyl;
$R^4$ is H;
$R^5$ is H;
or pharmaceutically acceptable salt, enantiomer or diastereomer thereof.

Another embodiment of present invention is that (vii) particular compounds of the present invention are the following:
3-(2-oxopyrrolidin-1-yl)-N-(3,4,5-trifluorophenyl)-4,5,6,7-tetrahydropyrazolo[1,5-a]pyridine-5-carboxamide;
3-(5,5-dimethyl-2-oxo-oxazolidin-3-yl)-N-(3,4,5-trifluorophenyl)-4,5,6,7-tetrahydropyrazolo[1,5-a]pyridine-5-carboxamide;
3-(2,4-difluorophenyl)-N-(3,4,5-trifluorophenyl)-4,5,6,7-tetrahydropyrazolo[1,5-a]pyridine-5-carboxamide;

3-cyclopentyl-N-(3,4,5-trifluorophenyl)-4,5,6,7-tetrahydropyrazolo[1,5-a]pyridine-5-carboxamide;
3-(1,1-dioxo-1,2-thiazolidin-2-yl)-N-(3,4,5-trifluorophenyl)-4,5,6,7-tetrahydropyrazolo[1,5-a]pyridine-5-carboxamide;
3-(5-benzyl-1,1-dioxo-1,2,5-thiadiazolidin-2-yl)-N-(3,4,5-trifluorophenyl)-4,5,6,7-tetrahydropyrazolo[1,5-a]pyridine-5-carboxamide;
3-(1,1-dioxo-1,2,5-thiadiazolidin-2-yl)-N-(3,4,5-trifluorophenyl)-4,5,6,7-tetrahydropyrazolo[1,5-a]pyridine-5-carboxamide;
3-(4-cyano-2-oxo-pyrrolidin-1-yl)-N-(3,4,5-trifluorophenyl)-4,5,6,7-tetrahydropyrazolo[1,5-a]pyridine-5-carboxamide;
3-(3-oxomorpholin-4-yl)-N-(3,4,5-trifluorophenyl)-4,5,6,7-tetrahydropyrazolo[1,5-a]pyridine-5-carboxamide;
3-[4-(3-methyl-1,2,4-oxadiazol-5-yl)-2-oxo-pyrrolidin-1-yl]-N-(3,4,5-trifluorophenyl)-4,5,6,7-tetrahydropyrazolo[1,5-a]pyridine-5-carboxamide;
3-(2,4-difluorophenyl)-N-(3-thienyl)-4,5,6,7-tetrahydropyrazolo[1,5-a]pyridine-5-carboxamide;
3-(2,4-difluorophenyl)-N-[4-fluoro-3-(trifluoromethyl)phenyl]-4,5,6,7-tetrahydropyrazolo[1,5-a]pyridine-5-carboxamide;
N-(3-cyano-4-fluoro-phenyl)-3-(2,4-difluorophenyl)-4,5,6,7-tetrahydropyrazolo[1,5-a]pyridine-5-carboxamide;
3-(2,4-difluorophenyl)-N-(4-fluoro-3-methyl-phenyl)-4,5,6,7-tetrahydropyrazolo[1,5-a]pyridine-5-carboxamide;
3-(2,4-difluorophenyl)-N-(2,6-difluoro-4-pyridyl)-4,5,6,7-tetrahydropyrazolo[1,5-a]pyridine-5-carboxamide;
3-(2,4-difluorophenyl)-N-(2-fluoro-4-pyridyl)-4,5,6,7-tetrahydropyrazolo[1,5-a]pyridine-5-carboxamide;
3-(6-fluoro-3-pyridyl)-N-(3,4,5-trifluorophenyl)-4,5,6,7-tetrahydropyrazolo[1,5-a]pyridine-5-carboxamide; and
3-[4-(5-methyl-1,2,4-oxadiazol-3-yl)-2-oxo-pyrrolidin-1-yl]-N-(3,4,5-trifluorophenyl)-4,5,6,7-tetrahydropyrazolo[1,5-a]pyridine-5-carboxamide.

Synthesis

The compounds of the present invention can be prepared by any conventional means. Suitable processes for synthesizing these compounds as well as their starting materials are provided in the schemes below and in the examples. All substituents, in particular, $R^1$ to $R^5$ are as defined above unless otherwise indicated. Furthermore, and unless explicitly otherwise stated, all reactions, reaction conditions, abbreviations and symbols have the meanings well known to a person of ordinary skill in organic chemistry.

Scheme 1: General synthetic route for Compounds of formula (Ia) and (Ib)

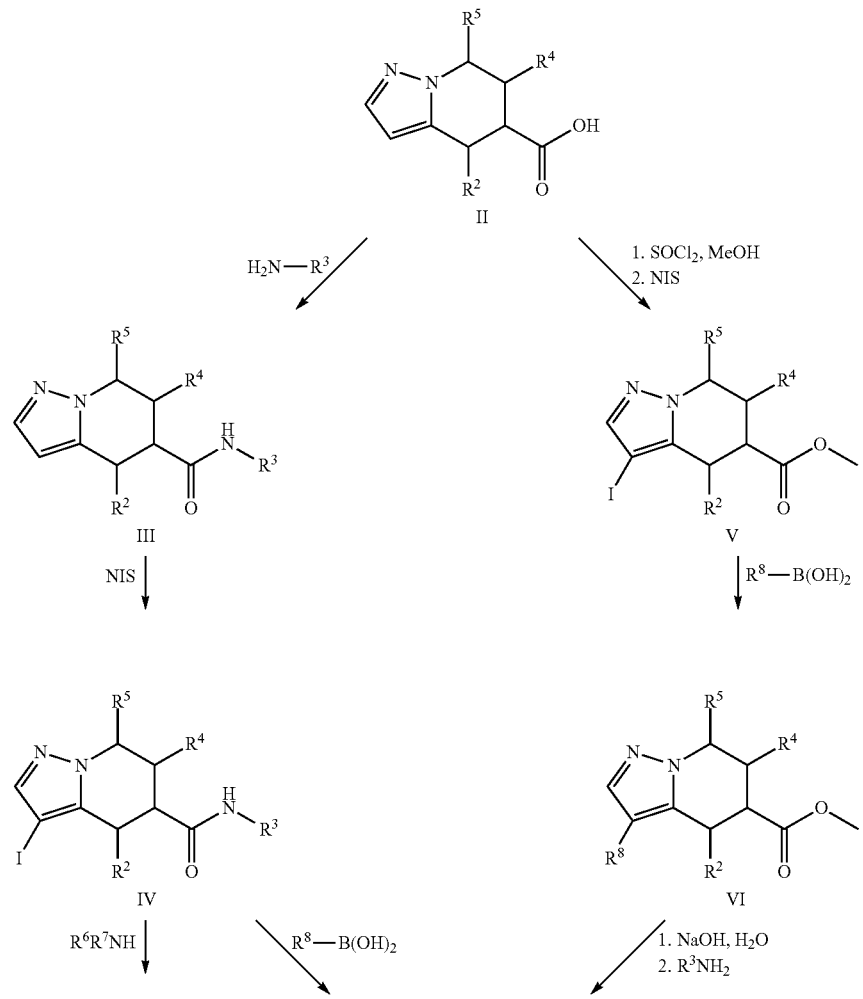

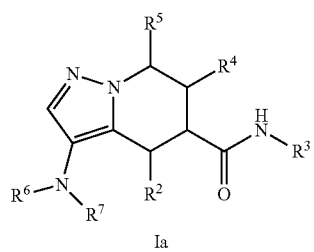

Ia

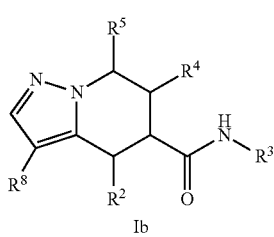

Ib

R$^1$ is R$^6$R$^7$N— or R$^8$. R$^6$ and R$^7$ together with the nitrogen atom they are attached to form a 3-7 membered heterocyclyl, such as, but not limited to, dioxothiadiazolidinyl, dioxothiazolidinyl, oxomorpholinyl, oxooxazolidinyl, oxopyrrolidinyl. R$^8$ is aryl, heteroaryl or C$_{3-7}$cycloalkyl. The compound of formula (Ia) or (Ib) can be prepared according to Scheme 1. Acid (II) reacts with amine R$^3$NH$_2$ in the presence of a coupling reagent, such as HATU, and a base, such as DIPEA, to give amide (III), which is treated with an iodinating reagent, such as N-iodosuccinimide, to give iodide (IV). Iodide (IV) undergoes copper catalyzed coupling reaction with R$^6$R$^7$NH in the presence of a copper catalyst, such as CuI, affords final compound of formula (Ia), or undergoes palladium catalyzed coupling reaction with boronic acid R$^8$—B(OH)$_2$ in the presence of a palladium catalyst, such as PdCl$_2$(dppf), affords final compound of formula (Ib). Another route used to synthesize compound of formula (Ib) starts with esterification of acid (II) followed by iodination to give ester (V), which reacts with R$^8$—B(OH)$_2$ in the presence of palladium catalyst, such as PdCl$_2$(dppf), to afford compound of formula (VI). Hydrolysis of compound of formula (VI) with a base, such as NaOH, gives an acid, which couples with amine R$^3$NH$_2$ in the presence of a coupling reagent, such as HATU, and a base, such as DIPEA, to give compound of formula (Ib). Or the acid from hydrolysis of compound of formula (VI) is converted to the corresponding acyl chloride, which reacts with amine R$^3$NH$_2$ to afford compound of formula (Ib).

This invention also relates to a process for the preparation of a compound of formula (I), (Ia) or (Ib) comprising any one of the following steps:
(a) the reaction of iodide (IV),

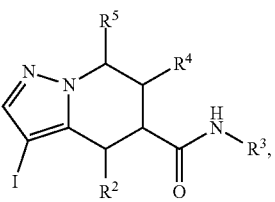

with R$^6$R$^7$NH in the presence of a copper catalyst;
(b) the reaction of iodide (IV),

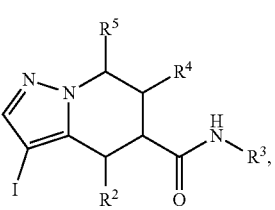

with boronic acid R$^1$—B(OH)$_2$ in the presence of a palladium catalyst;
(c) the reaction of a compound of formula (VI),

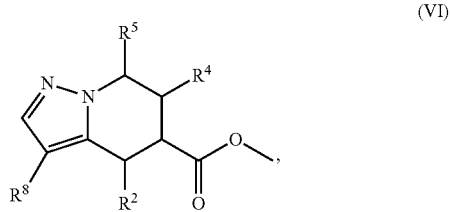

with a base followed by coupling with R$^3$NH$_2$ in the presence of a coupling reagent; wherein R$^2$, R$^3$, R$^4$, R$^5$ and R$^8$ are defined above.

In step (a), the copper catalyst can be for example CuI.

In step (b), the palladium catalyst can be for example PdCl$_2$(dppf).

In step (c), the coupling reagent can be for example HATU.

A compound of formula (I), (Ia) or (Ib) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 30 mg to 90 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Indications and Methods of Treatment

The compounds of the invention can inhibit HBV's DNA synthesis and reduce HBV DNA levels. Accordingly, the compounds of the invention are useful for the treatment or prophylaxis of HBV infection.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection which method comprises administering an effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations used herein are as follows:

| | |
|---|---|
| Ac$_2$O | Acetic anhydride |
| DIPEA: | N,N-diisopropylethylamine |
| EtOAc: | ethyl acetate |
| EC$_{50}$: | half maximal effective concentration |
| HATU: | O-(7-aza-1H-benzotriazole-1-yl)-N,N,N',N'-tetramethyluronium hexafluorophosphate |
| HPLC: | high performance liquid chromatography |
| MS (ESI): | mass spectroscopy (electron spray ionization) |
| NIS | N-iodosuccinimide |
| NMP | 1-methylpyrrolidin-2-one |
| obsd. | Observed |
| PdCl$_2$(dppf) | [1,1'-bis(diphenylphosphino)ferrocene]dichloropalladium(II) |
| Pd/C: | palladium on activated carbon |
| prep-HPLC: | preparative high performance liquid chromatography |
| prep-TLC: | preparative thin layer chromatography |
| TEA: | Triethylamine |

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 A, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). LC/MS spectra of compounds were obtained using a LC/MS (Waters™ Alliance 2795-Micromass ZQ). LC/MS conditions were as follows (running time 6 mins):

Acidic condition: A: 0.1% formic acid in $H_2O$; B: 0.1% formic acid in acetonitrile;

Basic condition: A: 0.1% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples are intended to illustrate the meaning of the present invention but should by no means represent a limitation within the meaning of the present invention:

PREPARATIVE EXAMPLES

The invention will be more fully understood by reference to the following examples. They should not, however, be construed as limiting the scope of the invention.

Example 1

3-(2-oxopyrrolidin-1-yl)-N-(3,4,5-trifluorophenyl)-4,5,6,7-tetrahydropyrazolo[1,5-a]pyridine-5-carboxamide

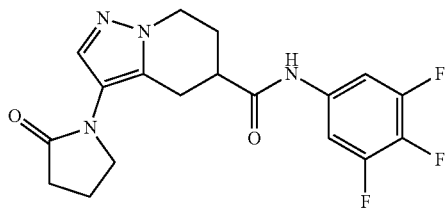 [SMILES: O=C(Nc1cc(F)c(F)c(F)c1)C1CCn2ncc(N3CCCC3=O)c2C1]

The title compound was prepared according to the following scheme:

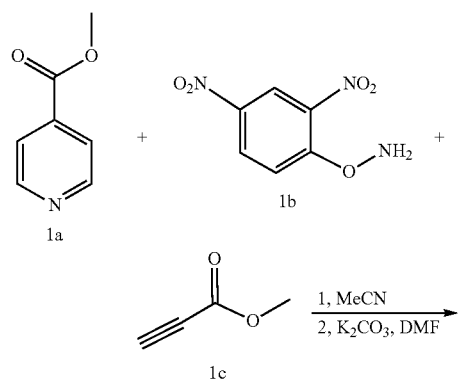

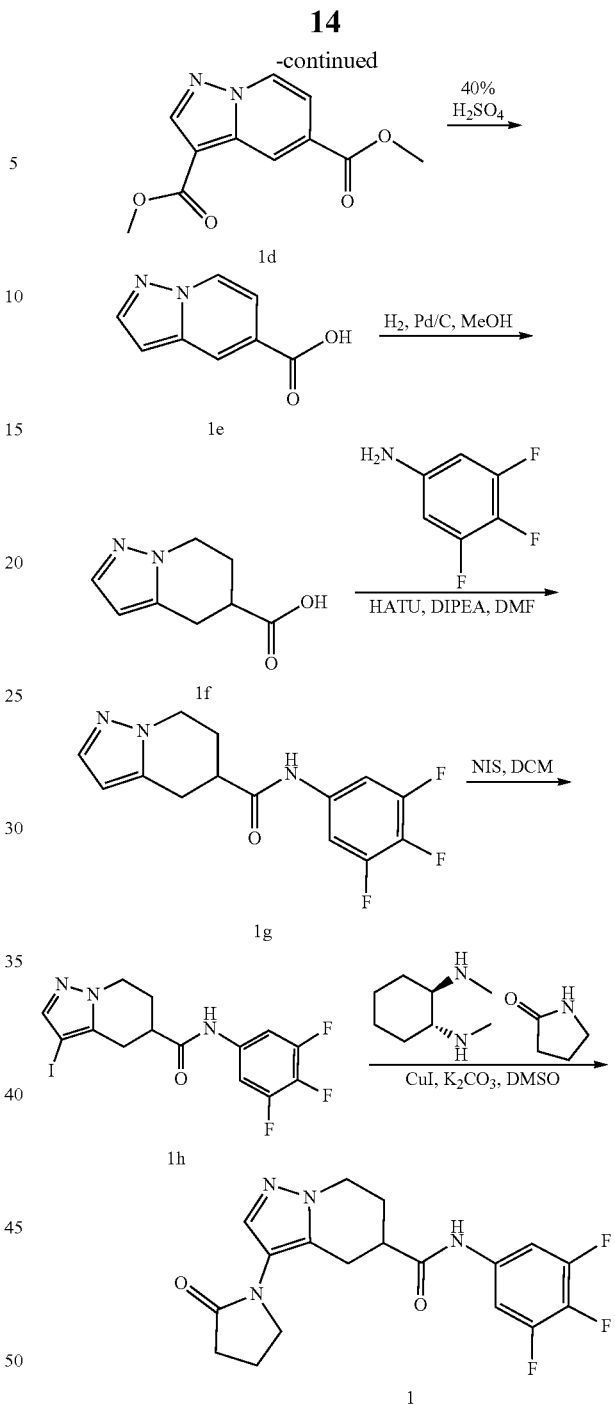

Step 1: Preparation of dimethyl pyrazolo[1,5-a]pyridine-3,5-dicarboxylate (Compound 1d)

A solution of methyl pyridine-4-carboxylate (compound 1a, 5.0 g, 36.5 mmol) and O-(2,4-dinitrophenyl)hydroxylamine (compound 1b, 7.3 g, 2.6 mmol) in MeCN (250 mL) was stirred at 40° C. for 18 hours. The reaction mixture was concentrated and dissolved in DMF (50 mL), followed by addition of methyl propiolate (compound 1c, 3.1 g, 36.5 mmol) and $K_2CO_3$ (10.1 g, 72.9 mmol). Then the reaction mixture was stirred at 25° C. for 4 hours, and diluted with EtOAc (300 mL). The resulting mixture was washed with brine (100 mL) for four times. The organic layer was dried over anhydrous Na$_2$SO$_4$ and concentrated under reduced pressure. The residue was purified by column chromatography to give dimethyl pyrazolo[1,5-a]pyridine-3,5-dicarboxylate (compound 1d, 5.1 g) as a brown solid. MS obsd. (ESI$^+$) [(M+H)$^+$]: 235.

Step 2: Preparation of pyrazolo[1,5-a]pyridine-5-carboxylic acid (Compound 1e)

A solution of dimethyl pyrazolo[1,5-a]pyridine-3,5-dicarboxylate (compound 1d, 2.0 g, 8.54 mmol) in sulfuric acid (40% in H$_2$O, 50 mL) was stirred at 100° C. for 4 hours. After being cooled to room temperature, the reaction mixture was adjusted to pH=4 with 2 N NaOH aqueous solution, and then extracted with EtOAc (100 mL) for 3 times. The combined organic layer was dried over anhydrous Na$_2$SO$_4$ and concentrated under reduced pressure to give pyrazolo[1,5-a]pyridine-5-carboxylic acid (compound 1e, 1.0 g, crude) as a brown solid. MS obsd. (ESI$^+$) [(M+H)$^+$]: 163.

Step 3: Preparation of 4,5,6,7-tetrahydropyrazolo[1,5-a]pyridine-5-carboxylic acid (Compound 1f)

To a solution of pyrazolo[1,5-a]pyridine-5-carboxylic acid (compound 1e, 1.0 g, 6.2 mmol) in MeOH (20 mL) was added Pd/C (200 mg). The reaction mixture was stirred at 60° C. for 12 hours under H$_2$ (50 psi), and then concentrated under reduced pressure to give 4,5,6,7-tetrahydropyrazolo[1,5-a]pyridine-5-carboxylic acid (compound 1f, 1.1 g, crude) as a brown oil. MS obsd. (ESI$^+$) [(M+H)$^+$]: 167.

Step 4: Preparation of N-(3,4,5-trifluorophenyl)-4,5,6,7-tetrahydropyrazolo[1,5-a]pyridine-5-carboxamide (Compound 1g)

To a solution of 4,5,6,7-tetrahydropyrazolo[1,5-a]pyridine-5-carboxylic acid (compound 1f, 1.0 g, 6.2 mmol), 3,4,5-trifluoroaniline (1.4 g, 9.3 mmol) and DIPEA (1.6 g, 12.3 mmol) in DMF (10 mL) was added HATU (3.5 g, 9.3 mmol). The reaction mixture was stirred at 25° C. for 12 hours, and then purified by prep-HPLC to give N-(3,4,5-trifluorophenyl)-4,5,6,7-tetrahydropyrazolo[1,5-a]pyridine-5-carboxamide (compound 1g, 1.1 g) as a yellow oil. MS obsd. (ESI$^+$) [(M+H)$^+$]: 296.

Step 5: Preparation of 3-iodo-N-(3,4,5-trifluorophenyl)-4,5,6,7-tetrahydropyrazolo[1,5-a]pyridine-5-carboxamide (Compound 1h)

To a solution of N-(3,4,5-trifluorophenyl)-4,5,6,7-tetrahydropyrazolo[1,5-a]pyridine-5-carboxamide (compound 1g, 500 mg, 1.7 mmol) in DCM (10 mL) was added NIS (571 mg, 2.5 mmol). The reaction mixture was stirred at 25° C. for 12 hours, and then partitioned between DCM (200 mL) and water (100 mL). The organic layer was washed with brine twice, dried over anhydrous Na$_2$SO$_4$ and concentrated under reduced pressure. The residue was purified by prep-HPLC to give 3-iodo-N-(3,4,5-trifluorophenyl)-4,5,6,7-tetrahydropyrazolo[1,5-a]pyridine-5-carboxamide (compound 1h, 610 mg) as a yellow solid. MS obsd. (ESI$^+$) [(M+H)$^+$]: 422.

Step 6: Preparation of 3-(2-oxopyrrolidin-1-yl)-N-(3,4,5-trifluorophenyl)-4,5,6,7-tetrahydropyrazolo[1,5-a]pyridine-5-carboxamide (Example 1)

To a mixture of 3-iodo-N-(3,4,5-trifluorophenyl)-4,5,6,7-tetrahydropyrazolo[1,5-a]pyridine-5-carboxamide (compound 1h, 100 mg, 0.24 mmol), pyrrolidin-2-one (30 mg, 0.36 mmol), trans-N,N'-dimethylcyclohexane-1,2-diamine (3 mg, 0.024 mmol) and CuI (45 mg, 0.24 mmol) in DMSO (3 mL) was added K$_2$CO$_3$ (131 mg, 0.95 mmol). The mixture was stirred at 110° C. for 12 hours, and then partitioned between EtOAc (50 mL) and water (50 mL). The organic layer was washed with brine, dried over anhydrous Na$_2$SO$_4$ and concentrated under reduced pressure. The residue was purified by prep-HPLC to give 3-(2-oxopyrrolidin-1-yl)-N-(3,4,5-trifluorophenyl)-4,5,6,7-tetrahydropyrazolo[1,5-a]pyridine-5-carboxamide (Example 1, 36 mg) as a white solid. $^1$H NMR (400 MHz, CDCl$_3$) δ 9.31 (br. s., 1H), 7.29-7.44 (m, 3H), 4.06-4.23 (m, 1H), 3.79-4.02 (m, 2H), 3.65 (m, 1H), 3.34 (d, 1H), 2.94-3.05 (m, 1H), 2.77 (dd, 4.77 Hz, 1H), 2.61-2.72 (m, 1H), 2.50-2.61 (m, 2H), 2.08-2.28 (m, 3H). MS obsd. (ESI$^+$) [(M+H)$^+$]: 379.

Example 2

3-(5,5-dimethyl-2-oxo-oxazolidin-3-yl)-N-(3,4,5-trifluorophenyl)-4,5,6,7-tetrahydropyrazolo[1,5-a]pyridine-5-carboxamide

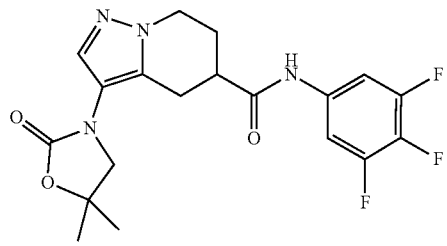 [SMILES: CC1(C)CN(c2cnn3c2CC(C(=O)Nc2cc(F)c(F)c(F)c2)CC3)C(=O)O1]

The title compound was prepared according to the following scheme:

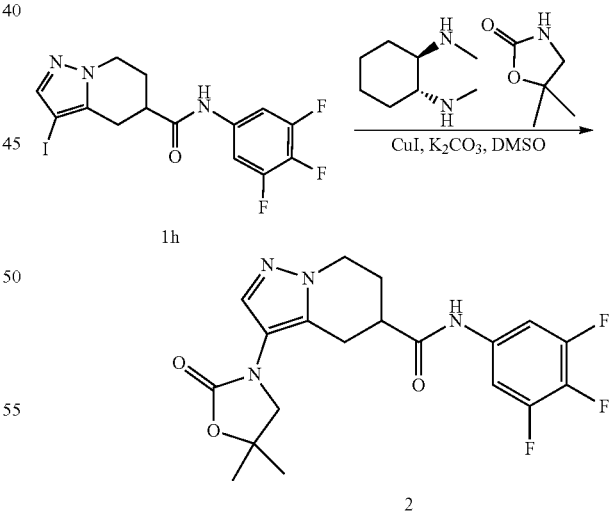

Preparation of 3-(5,5-dimethyl-2-oxo-oxazolidin-3-yl)-N-(3,4,5-trifluorophenyl)-4,5,6,7-tetrahydropyrazolo[1,5-a]pyridine-5-carboxamide To a mixture of 3-iodo-N-(3,4,5-trifluorophenyl)-4,5,6,7-tetrahydropyrazolo[1,5-a]pyridine-5-carboxamide (compound 1h, 100 mg, 0.24 mmol), 5,5-dimethyloxazolidin-2-one (41 mg, 0.36 mmol), trans-N,N'-dimethylcyclohexane-1,2-diamine (3 mg, 0.024 mmol) and CuI (45 mg, 0.24 mmol) in DMSO (3 mL) was added $K_2CO_3$ (131 mg, 0.95 mmol). The reaction mixture was stirred at 80° C. for 12 hours, and then partitioned between EtOAc (50 mL) and water (50 mL). The organic layer was washed with brine, dried over anhydrous $Na_2SO_4$ and concentrated under reduced pressure. The residue was purified by prep-HPLC to give 3-(5,5-dimethyl-2-oxo-oxazolidin-3-yl)-N-(3,4,5-trifluorophenyl)-4,5,6,7-tetrahydropyrazolo[1,5-a]pyridine-5-carboxamide (Example 2, 62 mg) as a white solid. $^1$H NMR (400 MHz, $CDCl_3$) δ 8.94 (br. s., 1H), 7.37-7.48 (m, 3H), 4.04-4.20 (m, 2H), 3.79 (d, 1H), 3.64 (d, 1H), 3.34 (dd, 1H), 2.89-3.04 (m, 2H), 2.58-2.70 (m, 1H), 2.20-2.33 (m, 1H), 1.61 (s, 6H). MS obsd. (ESI$^+$) [(M+H)$^+$]: 409.

Example 3

3-(2,4-difluorophenyl)-N-(3,4,5-trifluorophenyl)-4,5,6,7-tetrahydropyrazolo[1,5-a]pyridine-5-carboxamide

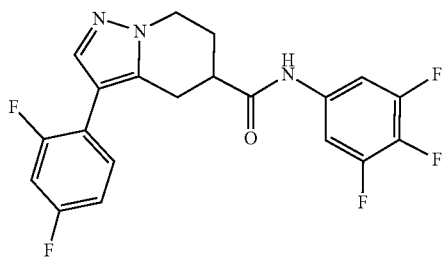 [SMILES: O=C(Nc1cc(F)c(F)c(F)c1)C1CCn2ncc(-c3ccc(F)cc3F)c2C1]

The title compound was prepared according to the following scheme:

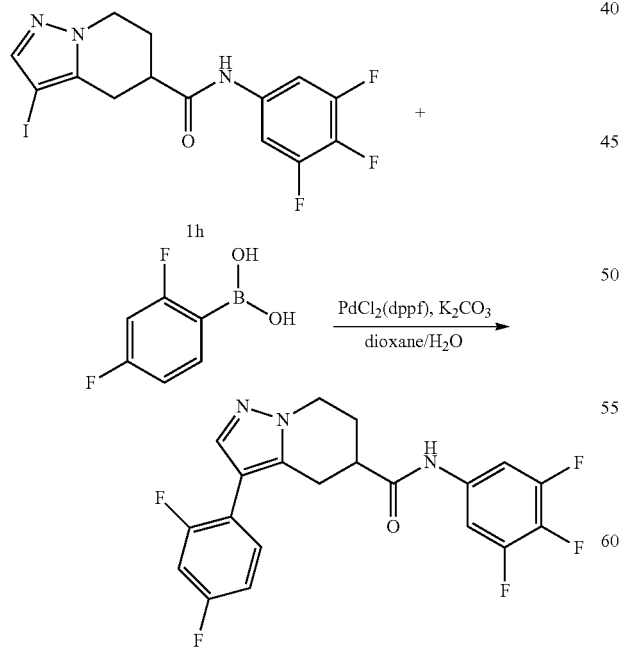

Preparation of 3-(2,4-difluorophenyl)-N-(3,4,5-trifluorophenyl)-4,5,6,7-tetrahydropyrazolo[1,5-a]pyridine-5-carboxamide To a mixture of 3-iodo-N-(3,4,5-trifluorophenyl)-4,5,6,7-tetrahydropyrazolo[1,5-a]pyridine-5-carboxamide (compound 1h, 100 mg, 0.24 mmol) and (2,4-difluorophenyl)boronic acid (38 mg, 0.24 mmol) in dioxane/$H_2O$ (3 mL/0.5 mL) was added $K_2CO_3$ (98 mg, 0.71 mmol) and $PdCl_2$(dppf) (18 mg, 0.024 mmol) under $N_2$ atmosphere. The reaction mixture was stirred at 80° C. for 12 hours, and then partitioned between EtOAc (100 mL) and water (50 mL). The organic layer was washed with brine, dried over anhydrous $Na_2SO_4$ and concentrated under reduced pressure. The residue was purified by prep-HPLC to give 3-(2,4-difluorophenyl)-N-(3,4,5-trifluorophenyl)-4,5,6,7-tetrahydropyrazolo[1,5-a]pyridine-5-carboxamide (Example 3, 41 mg) as a white solid. $^1$H NMR (400 MHz, $CDCl_3$) δ 7.66 (s, 1H), 7.38 (br. s., 1H), 7.29-7.34 (m, 2H), 6.88-6.99 (m, 2H), 4.49 (dt, 1H), 4.13-4.28 (m, 1H), 3.02-3.24 (m, 2H), 2.75 (m, 1H), 2.35-2.50 (m, 2H). MS obsd. (ESI$^+$) [(M+H)$^+$]: 408.

Example 4

3-cyclopentyl-N-(3,4,5-trifluorophenyl)-4,5,6,7-tetrahydropyrazolo[1,5-a]pyridine-5-carboxamide

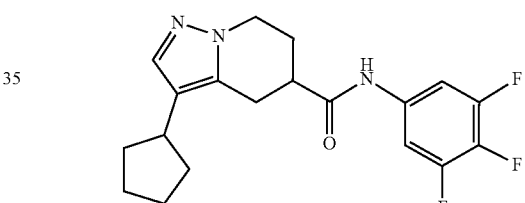

The title compound was prepared according to the following scheme:

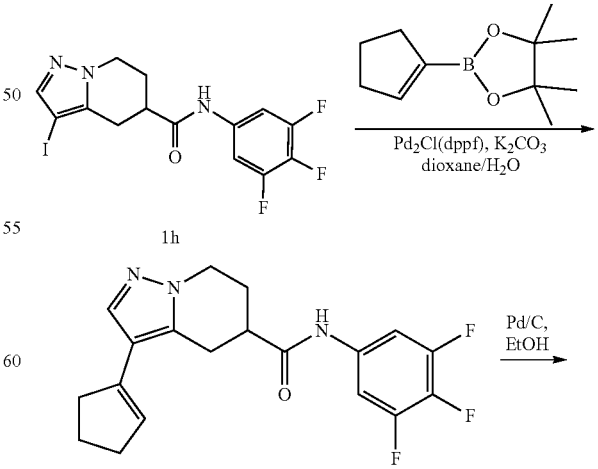

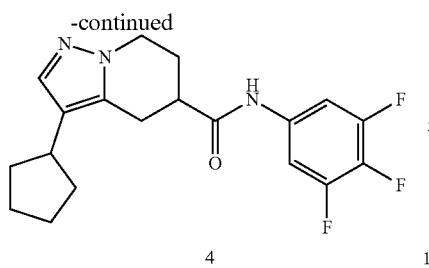

4

Step 1: Preparation of 3-(cyclopenten-1-yl)-N-(3,4,5-trifluorophenyl)-4,5,6,7-tetrahydropyrazolo[1,5-a]pyridine-5-carboxamide To a mixture of 3-iodo-N-(3,4,5-trifluorophenyl)-4,5,6,7-tetrahydropyrazolo[1,5-a]pyridine-5-carboxamide (compound 1h, 90 mg, 0.21 mmol) and 1-cyclopentenylboronic acid pinacol ester (50 mg, 0.26 mmol) in dioxane/H$_2$O (2 mL/0.4 mL) was added K$_2$CO$_3$ (89 mg, 0.64 mmol) and PdCl$_2$(dppf) (15 mg, 0.021 mmol) under N$_2$ atmosphere. The reaction mixture was stirred at 90° C. for 12 hours, and then diluted with EtOAc (100 mL). The resulting mixture was washed with water and brine, dried over anhydrous Na$_2$SO$_4$ and concentrated under reduced pressure. The residue was purified by prep-TLC to give compound 4a (60 mg) as a colorless oil. MS obsd. (ESI$^+$) [(M+H)$^+$]: 362.

Step 2: Preparation of 3-cyclopentyl-N-(3,4,5-trifluorophenyl)-4,5,6,7-tetrahydropyrazolo[1,5-a]pyridine-5-carboxamide A mixture of 3-(cyclopenten-1-yl)-N-(3,4,5-trifluorophenyl)-4,5,6,7-tetrahydropyrazolo[1,5-a]pyridine-5-carboxamide (compound 4a, 60 mg, 0.17 mmol) and Pd/C (10 mg) in ethanol (3 mL) was stirred at 25° C. under H$_2$ (15 psi) for 12 hours. The mixture was filtered, and the filtrate was concentrated under reduced pressure. The residue was purified by prep-HPLC to give 3-cyclopentyl-N-(3,4,5-trifluorophenyl)-4,5,6,7-tetrahydropyrazolo[1,5-a]pyridine-5-carboxamide (Example 4, 17 mg) as a white solid. $^1$H NMR (400 MHz, MeOD) δ 7.40-7.51 (m, 2H), 7.31 (s, 1H), 4.23-4.33 (m, 1H), 4.02-4.11 (m, 1H), 3.03-3.15 (m, 1H), 2.81-2.95 (m, 3H), 2.30-2.38 (m, 1H), 2.11-2.25 (m, 1H), 1.96-2.08 (m, 2H), 1.42-1.86 (m, 6H). MS obsd. (ESI$^+$) [(M+H)$^+$]: 364.

Example 5

3-(1,1-dioxo-1,2-thiazolidin-2-yl)-N-(3,4,5-trifluorophenyl)-4,5,6,7-tetrahydropyrazolo[1,5-a]pyridine-5-carboxamide

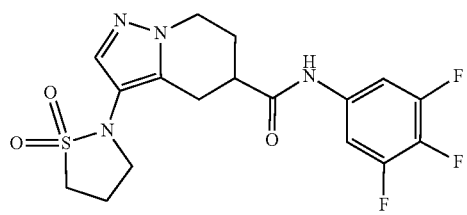 [SMILES: O=C(Nc1cc(F)c(F)c(F)c1)C1CCn2ncc(N3CCCS3(=O)=O)c2C1]

The title compound was prepared according to the following scheme:

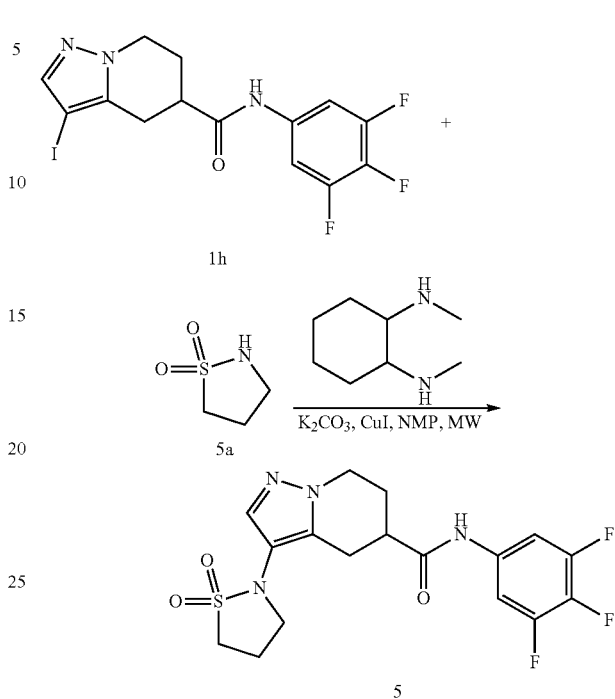

To a solution of 3-iodo-N-(3,4,5-trifluorophenyl)-4,5,6,7-tetrahydropyrazolo[1,5-a]pyridine-5-carboxamide (compound 1h, 20 mg, 0.048 mmol) in DMSO (1.0 mL) was added CuI (2 mg, 0.0095 mmol), K$_2$CO$_3$ (7 mg, 0.095 mmol), N,N'-dimethyl-1,2-cyclohexanediamine (2 mg, 0.0095 mmol), and 1,2-thiazolidine 1,1-dioxide (compound 5a, 5 mg, 0.057 mmol). The reaction mixture was stirred at 110° C. for 18 hours and then purified by flash chromatography and prep-HPLC to give 3-(1,1-dioxo-1,2-thiazolidin-2-yl)-N-(3,4,5-trifluorophenyl)-4,5,6,7-tetrahydropyrazolo[1,5-a]pyridine-5-carboxamide (Example 5, 11.5 mg) as a white solid. $^1$H NMR (400 MHz, CDCl$_3$) δ 8.21 (s, 1H), 7.56 (s, 1H), 7.41-7.26 (m, 2H), 4.27-4.14 (m, 1H), 4.07 (m, 1H), 3.73-3.54 (m, 2H), 3.36 (t, 2H), 3.25-3.08 (m, 2H), 2.84-2.72 (m, 1H), 2.60-2.39 (m, 3H), 2.34-2.21 (m, 1H). MS obsd. (ESI$^+$) [(M+H)$^+$]: 415

Example 6

3-(5-benzyl-1,1-dioxo-1,2,5-thiadiazolidin-2-yl)-N-(3,4,5-trifluorophenyl)-4,5,6,7-tetrahydropyrazolo[1,5-a]pyridine-5-carboxamide

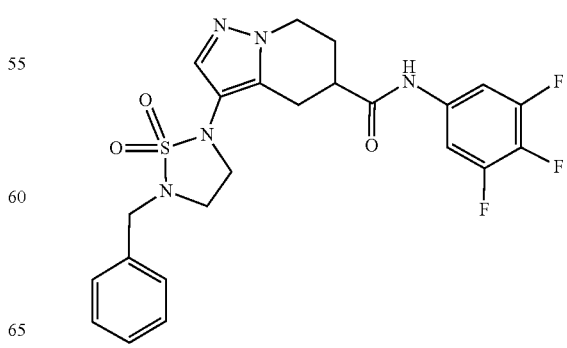

The title compound was prepared in analogy to the preparation of Example 5 by using 2-benzyl-1,2,5-thiadiazolidine 1,1-dioxide instead of 1,2-thiazolidine 1,1-dioxide (compound 5a). Example 6 was obtained as a white solid (10 mg). $^1$H NMR (400 MHz, CDCl$_3$) δ 8.52 (s, 1H), 7.61 (s, 1H), 7.41-7.29 (m, 7H), 4.38-4.28 (m, 1H), 4.27-4.15 (m, 2H), 4.04-3.90 (m, 1H), 3.73-3.60 (m, 2H), 3.43-3.28 (m, 2H), 3.25-3.01 (m, 2H), 2.61 (m, 1H), 2.37-2.19 (m, 2H). MS obsd. (ESI$^+$) [(M+H)$^+$]: 506.

Example 7

3-(1,1-dioxo-1,2,5-thiadiazolidin-2-yl)-N-(3,4,5-trifluorophenyl)-4,5,6,7-tetrahydropyrazolo[1,5-a]pyridine-5-carboxamide

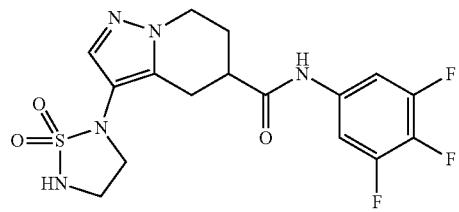 [SMILES: O=C(Nc1cc(F)c(F)c(F)c1)C1CCn2ncc(N3CCNS3(=O)=O)c2C1]

The title compound was prepared according to the following scheme:

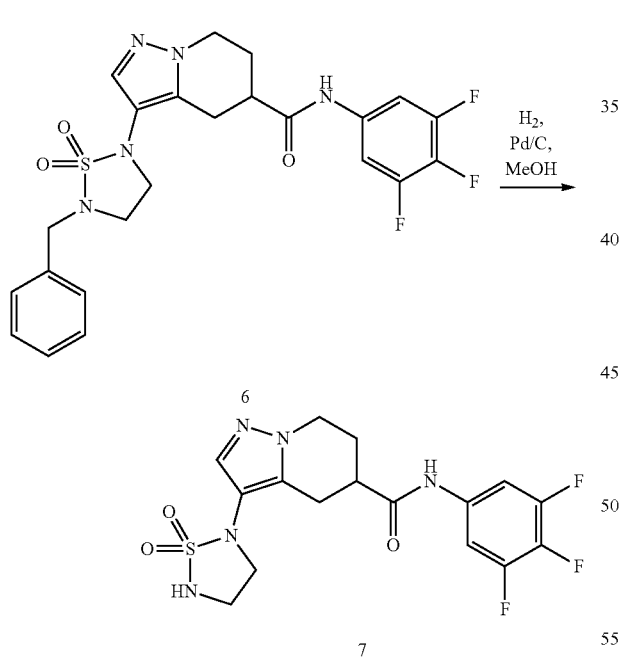

To a solution of 3-(5-benzyl-1,1-dioxo-1,2,5-thiadiazolidin-2-yl)-N-(3,4,5-trifluorophenyl)-4,5,6,7-tetrahydropyrazolo[1,5-a]pyridine-5-carboxamide (Example 6, 10 mg, 0.020 mmol) in methanol (15 mL) was added Pd/C (21 mg). The reaction mixture was stirred at 60° C. under H$_2$ atmosphere (50 psi) for 18 hours and then filtered, the filtrate was concentrated under reduced pressure. The residue was purified by prep-HPLC to give 3-(1,1-dioxo-1,2,5-thiadiazolidin-2-yl)-N-(3,4,5-trifluorophenyl)-4,5,6,7-tetrahydropyrazolo[1,5-a]pyridine-5-carboxamide (Example 7, 3.0 mg) as a white solid. $^1$H NMR (400 MHz, MeOD) δ 8.52 (br s, 1H), 7.58 (s, 1H), 7.49-7.27 (m, 2H), 4.39-4.22 (m, 1H), 4.10 (m, 1H), 3.84-3.70 (m, 2H), 3.60-3.47 (m, 2H), 3.25-3.13 (m, 1H), 3.06-2.95 (m, 1H), 2.89 (m, 1H), 2.39-2.17 (m, 2H). MS obsd. (ESI$^+$) [(M+H)$^+$]: 416.

Example 8

3-(4-cyano-2-oxo-pyrrolidin-1-yl)-N-(3,4,5-trifluorophenyl)-4,5,6,7-tetrahydropyrazolo[1,5-a]pyridine-5-carboxamide

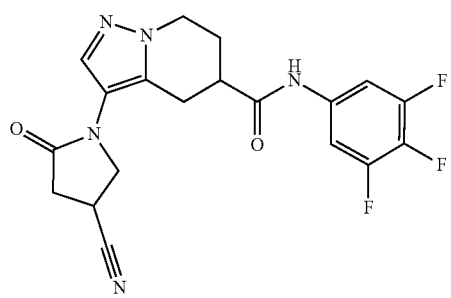 [SMILES: N#CC1CC(=O)N(c2cnn3c2CC(C(=O)Nc2cc(F)c(F)c(F)c2)CC3)C1]

The title compound was prepared according to the following scheme:

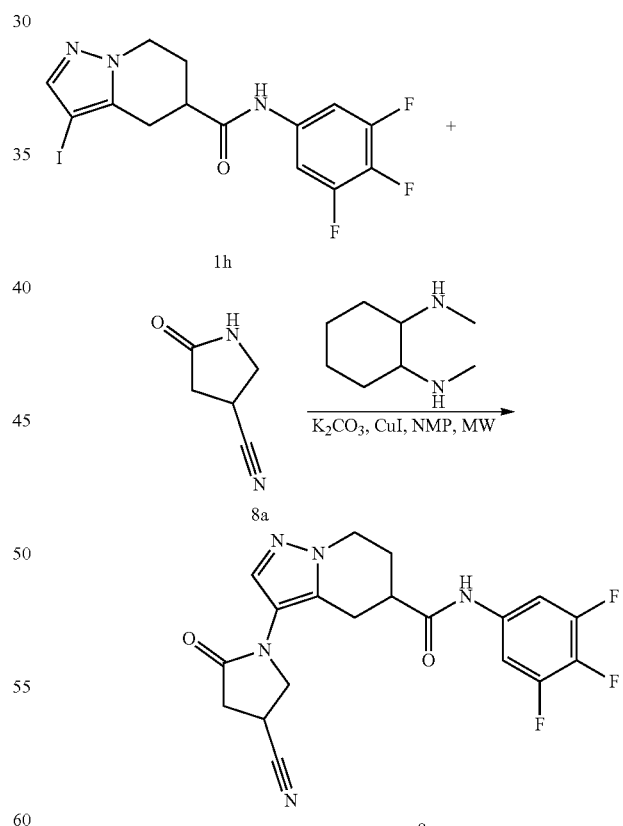

To a solution of 3-iodo-N-(3,4,5-trifluorophenyl)-4,5,6,7-tetrahydropyrazolo[1,5-a]pyridine-5-carboxamide (compound 1h, 100 mg, 0.24 mmol) in NMP (1 mL) was added 5-oxopyrrolidine-3-carbonitrile (31 mg, 0.28 mmol), N,N'-dimethyl-1,2-cyclohexanediamine (6.7 mg, 0.05 mmol), potassium phosphate (151 mg, 0.71 mmol) and CuI (4.5 mg, 0.02 mmol). The resulting mixture was heated under microwave at 110° C. for 2 hours. The mixture was purified by column chromatography and prep-HPLC to give 3-(4-cyano-2-oxo-pyrrolidin-1-yl)-N-(3,4,5-trifluorophenyl)-4,5,6,7-tetrahydropyrazolo[1,5-a]pyridine-5-carboxamide (Example 8, 13 mg) as a white solid. $^1$H NMR (400 MHz, MeOD) δ 7.55 (s, 1H), 7.50-7.38 (m, 2H), 4.30 (m, 1H), 4.16-3.92 (m, 3H), 3.79-3.66 (m, 1H), 3.08-2.76 (m, 5H), 2.40-2.31 (m, 1H), 2.25 (m, 1H). MS obsd. (ESI$^+$) [(M+H)$^+$]: 404.

Example 9

3-(3-oxomorpholin-4-yl)-N-(3,4,5-trifluorophenyl)-4,5,6,7-tetrahydropyrazolo[1,5-a]pyridine-5-carboxamide

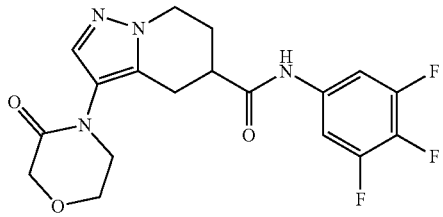 [SMILES: O=C(Nc1cc(F)c(F)c(F)c1)C1CCn2ncc(N3CCOCC3=O)c2C1]

The title compound was prepared in analogy to the preparation of Example 5 by using morpholin-3-one instead of 1,2-thiazolidine 1,1-dioxide (compound 5a). Example 9 was obtained as a white solid (11 mg). $^1$H NMR (400 MHz, CDCl$_3$) δ 9.14 (s, 1H), 7.49-7.37 (m, 3H), 4.37 (s, 2H), 4.30-4.19 (m, 1H), 4.14-3.96 (m, 3H), 3.95-3.83 (m, 1H), 3.73-3.64 (m, 1H), 3.29-3.23 (m, 1H), 3.11 (m, 1H), 2.87-2.73 (m, 2H), 2.33-2.20 (m, 1H). MS obsd. (ESI$^+$) [(M+H)$^+$]: 395.

Example 10

3-[4-(3-methyl-1,2,4-oxadiazol-5-yl)-2-oxo-pyrrolidin-1-yl]-N-(3,4,5-trifluorophenyl)-4,5,6,7-tetrahydropyrazolo[1,5-a]pyridine-5-carboxamide

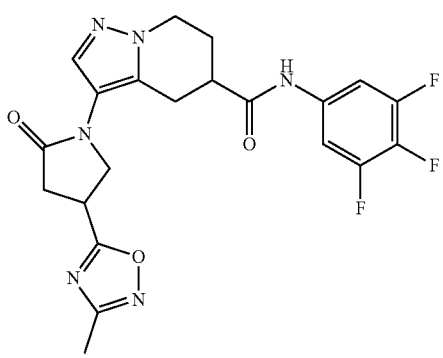 [SMILES: Cc1noc(C2CC(=O)N(c3cnn4c3CC(C(=O)Nc3cc(F)c(F)c(F)c3)CC4)C2)n1]

The title compound was prepared according to the following scheme:

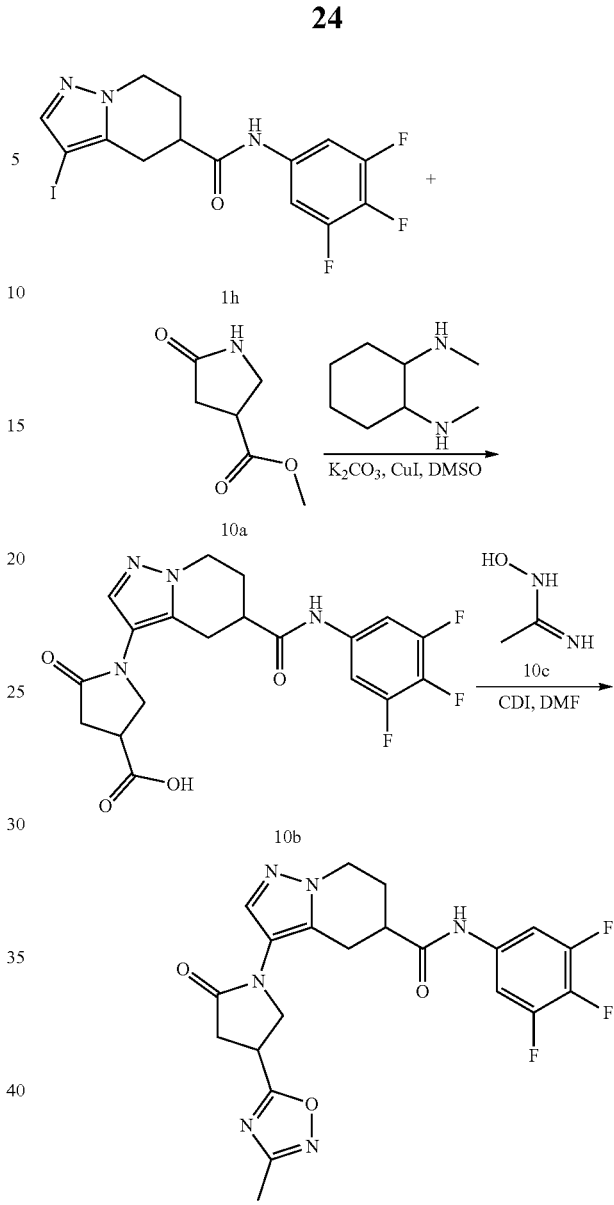

Step 1: Preparation of 5-oxo-1-[5-[(3,4,5-trifluorophenyl)carbamoyl]-4,5,6,7-tetrahydropyrazolo[1,5-a]pyridin-3-yl]pyrrolidine-3-carboxylic acid (Compound 10b)

To a solution of 3-iodo-N-(3,4,5-trifluorophenyl)-4,5,6,7-tetrahydropyrazolo[1,5-a]pyridine-5-carboxamide (compound 1h, 500 mg, 1.2 mmol) in DMSO (5 mL) was added methyl 5-oxopyrrolidine-3-carboxylate (204 mg, 1.4 mmol), N,N'-dimethyl-1,2-cyclohexanediamine (34 mg, 0.24 mmol), potassium carbonate (492 mg, 3.6 mmol) and CuI (0.01 mL, 0.24 mmol). The resulting mixture was stirred at 110° C. for 18 hour under N$_2$ atmosphere, and then purified by prep-HPLC to give compound 10b (100 mg) as an off-white solid. MS obsd. (ESI$^+$) [(M+H)$^+$]: 423.

Step 2: Preparation of 3-[4-(3-methyl-1,2,4-oxadiazol-5-yl)-2-oxo-pyrrolidin-1-yl]-N-(3,4,5-trifluorophenyl)-4,5,6,7-tetrahydropyrazolo[1,5-a]pyridine-5-carboxamide To a solution of 5-oxo-1-[5-[(3,4,5-trifluorophenyl)carbamoyl]-4,5,6,7-tetrahydropyrazolo[1,5-a]pyridin-3-yl]pyrrolidine-3-carboxylic acid (compound 10b, 15 mg, 0.04 mmol) in DMF (0.5 mL) was added CDI (6.9 mg, 0.04 mmol). The mixture was stirred at 100° C. for 1 hour, followed by addition of N-hydroxyacetamidine (4 mg, 0.05 mmol). The resulting mixture was stirred at 100° C. for 17 hours, and then purified by prep-HPLC to give 3-[4-(3-methyl-1,2,4-oxadiazol-5-yl)-2-oxo-pyrrolidin-1-yl]-N-(3,4,5-trifluorophenyl)-4,5,6,7-tetrahydropyrazolo[1,5-a]pyridine-5-carboxamide (Example 10, 7 mg) as a white solid. $^1$H NMR (400 MHz, MeOD) δ 7.55 (s, 1H), 7.48-7.38 (m, 2H), 4.33-4.18 (m, 2H), 4.16-3.96 (m, 3H), 3.12-2.83 (m, 6H), 2.38-2.34 (m, 3H), 2.29-2.19 (m, 1H). MS obsd. (ESI$^+$) [(M+H)$^+$]: 461.

Example 11

3-(2,4-difluorophenyl)-N-(3-thienyl)-4,5,6,7-tetrahydropyrazolo[1,5-a]pyridine-5-carboxamide

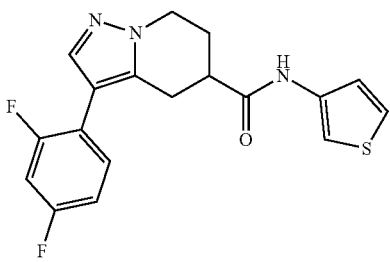 [SMILES: O=C(Nc1ccsc1)C1CCn2ncc(-c3ccc(F)cc3F)c2C1]

The title compound was prepared according to the following scheme:

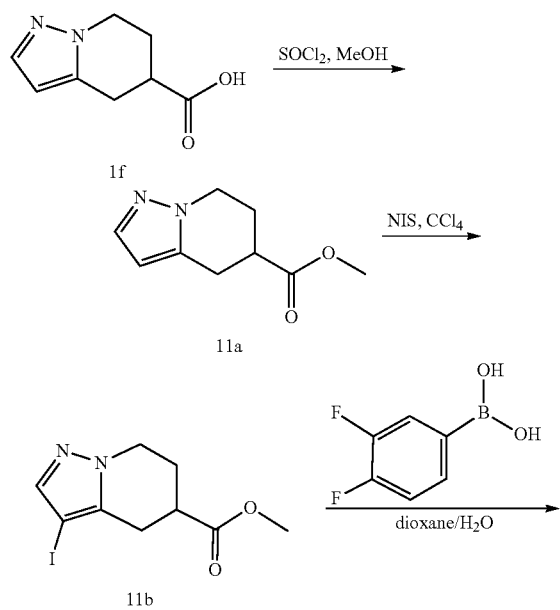

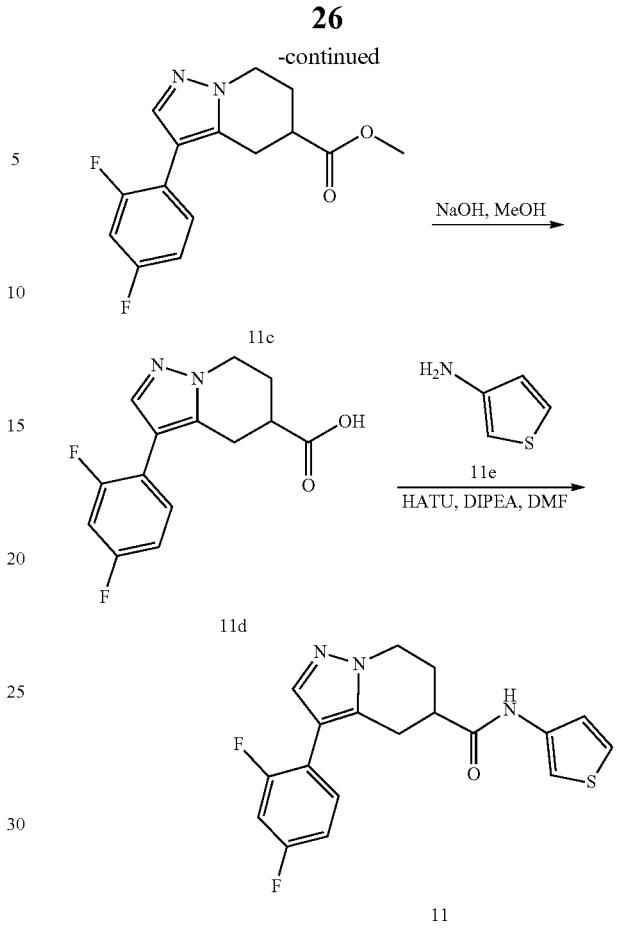

Step 1: Preparation of methyl 4,5,6,7-tetrahydropyrazolo[1,5-a]pyridine-5-carboxylate (Compound 11a)

A mixture of 4,5,6,7-tetrahydropyrazolo[1,5-a]pyridine-5-carboxylic acid (compound 1f, 100 mg, 0.60 mmol) and SOCl$_2$ (143 mg, 1.20 mmol) in MeOH (3 mL) was stirred at 70° C. for 16 hours. After the reaction mixture was concentrated under reduced pressure, the residue was diluted with DCM (50 mL) and washed with aqueous NaHCO$_3$ solution (20 mL) and brine (20 mL), dried over anhydrous Na$_2$SO$_4$, concentrated under reduced pressure to give crude methyl 4,5,6,7-tetrahydropyrazolo[1,5-a]pyridine-5-carboxylate (compound 11a, 100 mg) as a yellow oil, which was used directly in the next step without further purification. MS obsd. (ESI$^+$) [(M+H)$^+$]: 181.

Step 2: Preparation of methyl 3-iodo-4,5,6,7-tetrahydropyrazolo[1,5-a]pyridine-5-carboxylate (Compound 11b)

To a mixture of methyl 4,5,6,7-tetrahydropyrazolo[1,5-a]pyridine-5-carboxylate (compound 11a, crude 100 mg, 0.56 mmol) in CCl$_4$ (3 mL) was added NIS (213 mg, 0.95 mmol). The reaction mixture was stirred at 15° C. for 16 hours, and then partitioned between DCM (50 mL) and water (20 mL). The organic layer was washed with brine (30 mL), dried over anhydrous Na$_2$SO$_4$ and concentrated under reduced pressure. The residue was purified by prep-TLC to give methyl 3-iodo-4,5,6,7-tetrahydropyrazolo[1,5-a]pyridine-5-carboxylate (compound 1b, 130 mg) as a yellow oil. MS obsd. (ESI$^+$) [(M+H)$^+$]: 307.

Step 3: Preparation of methyl 3-(2,4-difluorophenyl)-4,5,6,7-tetrahydropyrazolo[1,5-a]pyridine-5-carboxylate (Compound 1c)

A mixture of methyl 3-iodo-4,5,6,7-tetrahydropyrazolo[1,5-a]pyridine-5-carboxylate (compound 1b, 120 mg, 0.39 mmol) and 2,4-difluorophenylboronic acid (68 mg, 0.43 mmol), $K_2CO_3$ (162 mg, 1.18 mmol) and $PdCl_2(dppf)$ (10 mg) in dioxane/$H_2O$ (4 mL/0.8 mL) was stirred at 80° C. for 16 hours. The reaction mixture was partitioned between EtOAc (100 mL) and water (30 mL). The organic layer was washed with brine (30 mL), dried over anhydrous $Na_2SO_4$ and concentrated under reduced pressure. The residue was purified by prep-TLC to give methyl 3-(2,4-difluorophenyl)-4,5,6,7-tetrahydropyrazolo[1,5-a]pyridine-5-carboxylate (compound 11c, 100 mg) as a colorless oil. MS obsd. (ESI⁺) [(M+H)⁺]: 293.

Step 4: Preparation of 3-(2,4-difluorophenyl)-4,5,6,7-tetrahydropyrazolo[1,5-a]pyridine-5-carboxylic Acid (Compound 11d)

To a mixture of methyl 3-(2,4-difluorophenyl)-4,5,6,7-tetrahydropyrazolo[1,5-a]pyridine-5-carboxylate (compound 11c, 100 mg, 0.34 mmol) in MeOH (2 mL) was added 2 N aqueous NaOH solution (0.34 mL). The mixture was stirred at 15° C. for 16 hours, and then acidified with 2 N aqueous HCl to pH=4. The resulting mixture was concentrated and partitioned between EtOAc (50 mL) and brine (20 mL). The organic layer was dried over anhydrous $Na_2SO_4$ and concentrated under reduced pressure to give 3-(2,4-difluorophenyl)-4,5,6,7-tetrahydropyrazolo[1,5-a]pyridine-5-carboxylic acid (compound 11d, 50 mg) as a white solid. MS obsd. (ESI⁺) [(M+H)⁺]: 279.

Step 5: Preparation of 3-(2,4-difluorophenyl)-N-(3-thienyl)-4,5,6,7-tetrahydropyrazolo[1,5-a]pyridine-5-carboxamide (Example 11)

To a mixture of 3-(2,4-difluorophenyl)-4,5,6,7-tetrahydropyrazolo[1,5-a]pyridine-5-carboxylic acid (compound 11d, 25 mg, 0.090 mmol), thiophen-3-amine (compound 11e, 11 mg, 0.11 mmol) and DIPEA (35 mg, 0.27 mmol) in DMF (0.5 mL) was added HATU (51 mg, 0.14 mmol). The reaction mixture was stirred at 15° C. for 16 hours, and then partitioned between EtOAc (50 mL) and water (20 mL). The organic layer was washed with brine, dried over anhydrous $Na_2SO_4$ and concentrated under reduced pressure. The residue was purified by prep-HPLC to give 3-(2,4-difluorophenyl)-N-(3-thienyl)-4,5,6,7-tetrahydropyrazolo[1,5-a]pyridine-5-carboxamide (Example 11, 5.0 mg) as a white solid. ¹H NMR (400 MHz, CDCl₃) δ ppm 7.86 (br s, 1H) 7.57-7.71 (m, 2H) 7.22-7.29 (m, 2H) 7.01 (d, 1H) 6.85-6.97 (m, 2H) 4.41-4.53 (m, 1H) 4.10-4.23 (m, 1H) 3.02-3.25 (m, 2H) 2.74 (m, 1H) 2.35-2.47 (m, 2H). MS obsd. (ESI⁺)[(M+H)⁺]: 360.

Example 12

3-(2,4-difluorophenyl)-N-[4-fluoro-3-(trifluoromethyl)phenyl]-4,5,6,7-tetrahydropyrazolo[1,5-a]pyridine-5-carboxamide

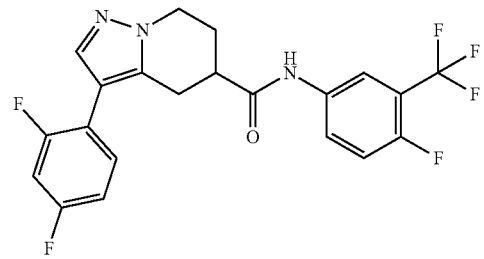 [SMILES: O=C(Nc1ccc(F)c(C(F)(F)F)c1)C1CCn2ncc(-c3ccc(F)cc3F)c2C1]

The title compound was prepared in analogy to the preparation of Example 11 by using 4-fluoro-3-(trifluoromethyl) aniline instead of thiophen-3-amine (compound 11e). Example 12 was obtained as a white solid (14 mg). ¹H NMR (400 MHz, CDCl₃) δ ppm 7.83 (br d, 1H), 7.73 (br d, 1H), 7.66 (s, 1H), 7.42 (br s, 1H), 7.26-7.33 (m, 1H), 7.19 (t, 1H), 6.86-6.96 (m, 2H), 4.49 (dt, 1H), 4.16-4.26 (m, 1H), 3.04-3.25 (m, 2H), 2.79 (br d, 1H), 2.36-2.49 (m, 2H). MS obsd (ESI) [(M+H)⁺]: 440

Example 13

N-(3-cyano-4-fluoro-phenyl)-3-(2,4-difluorophenyl)-4,5,6,7-tetrahydropyrazolo[1,5-a]pyridine-5-carboxamide

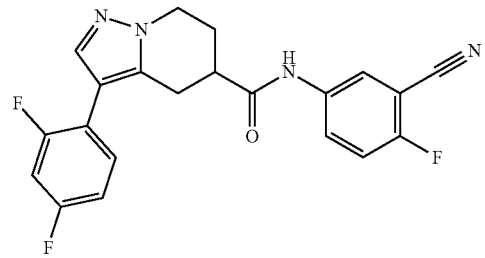 [SMILES: N#Cc1cc(NC(=O)C2CCn3ncc(-c4ccc(F)cc4F)c3C2)ccc1F]

The title compound was prepared in analogy to the preparation of Example 11 by using 5-amino-2-fluoro-benzonitrile instead of thiophen-3-amine (compound 11e). Example 13 was obtained as a white solid (23 mg). ¹H NMR (400 MHz, CDCl₃) δ ppm 7.93 (dd, 1H), 7.71-7.77 (m, 1H), 7.65 (s, 1H), 7.61 (s, 1H), 7.20-7.32 (m, 2H), 6.85-6.97 (m, 2H), 4.48 (dt, 1H), 4.15-4.26 (m, 1H), 3.03-3.22 (m, 2H), 2.74-2.84 (m, 1H), 2.38-2.47 (m, 2H). MS obsd (ESI) [(M+H)⁺]: 397

Example 14

3-(2,4-difluorophenyl)-N-(4-fluoro-3-methyl-phenyl)-4,5,7-tetrahydropyrazolo[1,5-a]pyridine-5-carboxamide

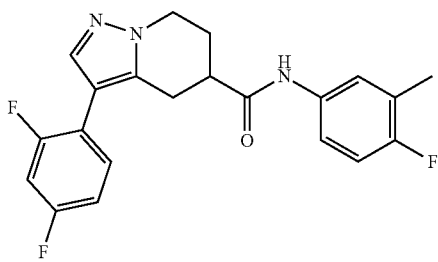 [SMILES: Cc1cc(NC(=O)C2CCn3ncc(-c4ccc(F)cc4F)c3C2)ccc1F]

The title compound was prepared in analogy to the preparation of Example 11 by using 4-fluoro-3-methyl-aniline instead of thiophen-3-amine (compound 11e). Example 14 was obtained as a white solid (8 mg). $^1$H NMR (400 MHz, CDCl$_3$) δ ppm 7.66 (s, 1H), 7.41 (br d, 1H), 7.18-7.33 (m, 3H), 6.88-7.00 (m, 3H), 4.45-4.53 (m, 1H), 4.16-4.25 (m, 1H), 3.14-3.25 (m, 1H), 3.03-3.12 (m, 1H), 2.69-2.79 (m, 1H), 2.38-2.46 (m, 2H), 2.27 (d, 3H). MS obsd (ESI) [(M+H)$^+$]: 386

Example 15

3-(2,4-difluorophenyl)-N-(2,6-difluoro-4-pyridyl)-4,5,6,7-tetrahydropyrazolo[1,5-a]pyridine-5-carboxamide

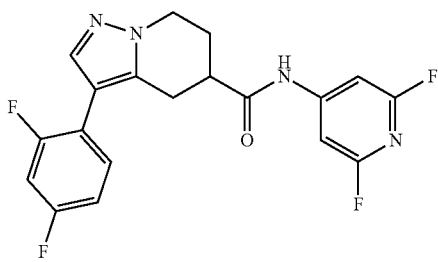 [SMILES: O=C(Nc1ccnc(F)c1)C1CCn2ncc(-c3ccc(F)cc3F)c2C1]

The title compound was prepared according to the following scheme:

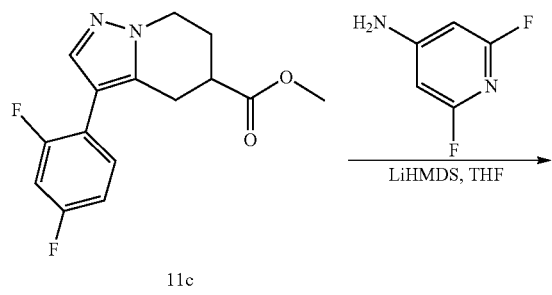

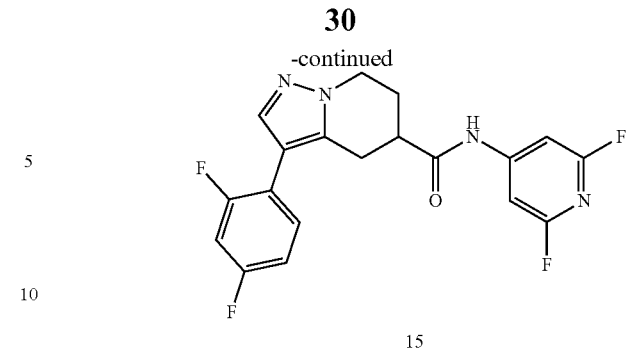

To a mixture of methyl 3-(2,4-difluorophenyl)-4,5,6,7-tetrahydropyrazolo[1,5-a]pyridine-5-carboxylate (compound 11c, 50 mg, 0.17 mmol) and 2,6-difluoropyridin-4-amine (26.7 mg, 0.21 mmol) in THF (1 mL) was added Lithium bis(trimethylsilyl) amide (0.26 mL, 0.26 mmol) at 0° C. The reaction mixture was stirred at 20° C. for 12 hours, and then quenched by addition of saturated aqueous NH$_4$Cl solution. The resulting mixture was extracted with EtOAc (5 mL) for three times. The combined organic layer was washed with brine, dried over anhydrous Na$_2$SO$_4$ and concentrated under reduced pressure. The residue was purified by prep-HPLC to afford 3-(2,4-difluorophenyl)-N-(2,6-difluoro-4-pyridyl)-4,5,6,7-tetrahydropyrazolo[1,5-a]pyridine-5-carboxamide (Example 15, 3 mg) as a white solid. $^1$H NMR (400 MHz, MeOD) δ 7.63 (d, 1H), 7.38-7.47 (m, 1H), 7.19 (s, 2H), 6.97-7.08 (m, 2H), 4.35-4.45 (m, 1H), 4.18 (td, 1H), 3.03-3.16 (m, 2H), 2.91-3.00 (m, 1H), 2.39-2.48 (m, 1H), 2.24-2.37 (m, 1H). MS obsd. (ESI$^+$)[(M+H)$^+$]: 391

Example 16

3-(2,4-difluorophenyl)-N-(2-fluoro-4-pyridyl)-4,5,6,7-tetrahydropyrazolo[1,5-a]pyridine-5-carboxamide

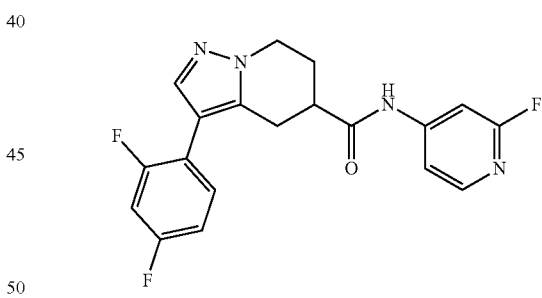

The title compound was prepared according to the following scheme:

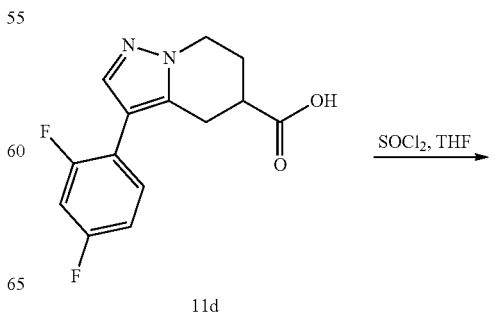

-continued

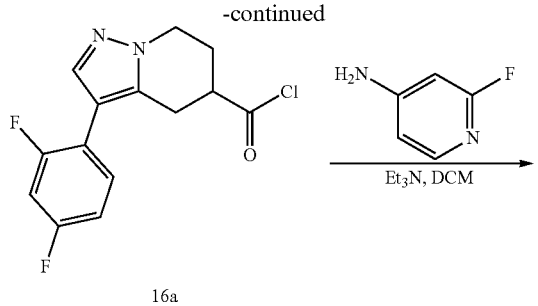

16a

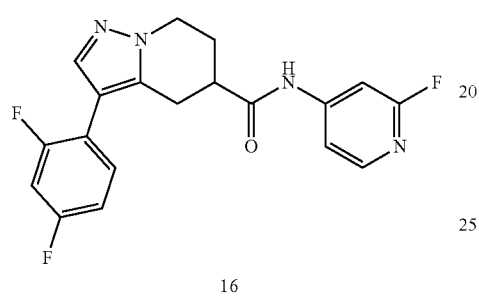

16

Step 1: Preparation of 3-(2,4-difluorophenyl)-4,5,6,7-tetrahydropyrazolo[1,5-a]pyridine-5-carbonyl chloride (Compound 16a)

To a stirred solution of 3-(2,4-difluorophenyl)-4,5,6,7-tetrahydropyrazolo[1,5-a]pyridine-5-carboxylic acid (compound 11d, 100.0 mg, 0.360 mmol) in THF (2 mL) was added thionyl chloride (213.78 mg, 1.8 mmol) slowly at 20° C. The mixture was stirred at 60° C. for 4 hours, and then concentrated under reduced pressure to give 3-(2,4-difluorophenyl)-4,5,6,7-tetrahydropyrazolo[1,5-a]pyridine-5-carbonyl chloride (compound 16a, 100 mg, crude), which was used directly for the next step.

Step 2: Preparation of 3-(2,4-difluorophenyl)-N-(2-fluoro-4-pyridyl)-4,5,6,7-tetrahydropyrazolo[1,5-a]pyridine-5-carboxamide (Example 16)

To a solution of 4-amino-2-fluoropyridine (19.8 mg, 0.18 mmol) and triethylamine (0.05 mL, 0.35 mmol) in DCM (1 mL) was added a solution of 3-(2,4-difluorophenyl)-4,5,6,7-tetrahydropyrazolo[1,5-a]pyridine-5-carbonyl chloride (compound 16a, 35.0 mg, 0.12 mmol) in DCM (1 mL). The reaction mixture was stirred at 20° C. for 12 hours, and then concentrated under reduced pressure. The residue was purified by prep-HPLC (formic acid as additive in eluent) to afford 3-(2,4-difluorophenyl)-N-(2-fluoro-4-pyridyl)-4,5,6,7-tetrahydropyrazolo[1,5-a]pyridine-5-carboxamide (Example 16, 10.6 mg) as its formic acid salt. $^1$H NMR (400 MHz, MeOD) δ 8.52 (br, 1H), 8.05 (d, 1H), 7.64 (d, 1H), 7.49 (d, 1H), 7.39-7.47 (m, 1H), 7.33-7.39 (m, 1H), 6.98-7.08 (m, 2H), 4.36-4.44 (m, 1H), 4.12-4.24 (m, 1H), 3.06-3.14 (m, 2H), 2.92-3.02 (m, 1H), 2.39-2.48 (m, 1H), 2.28-2.37 (m, 1H). MS obsd. (ESI$^+$) [(M+H)$^+$]: 373.

Example 17

3-(6-fluoro-3-pyridyl)-N-(3,4,5-trifluorophenyl)-4,5,6,7-tetrahydropyrazolo[1,5-a]pyridine-5-carboxamide

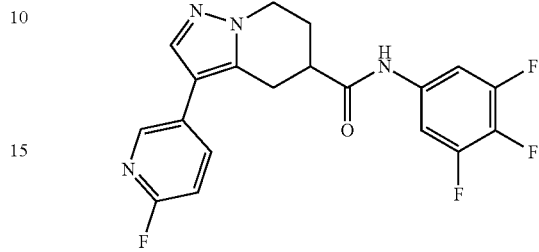

The title compound was prepared according to the following scheme:

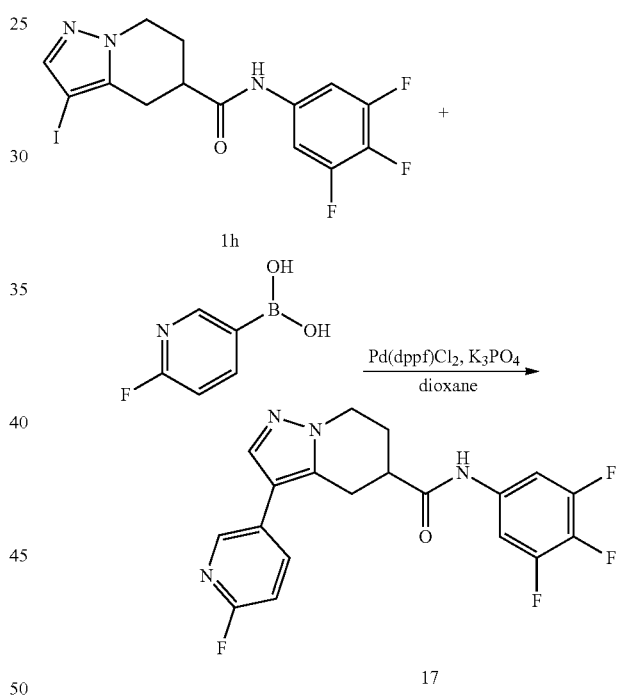

17

To a solution of 3-iodo-N-(3,4,5-trifluorophenyl)-4,5,6,7-tetrahydropyrazolo[1,5-a]pyridine-5-carboxamide (compound 1h, 20 mg, 0.05 mmol) in dioxane (0.5 mL) was added 2-fluoropyridine-5-boronic acid (13 mg, 0.09 mmol), K$_3$PO$_4$ (30 mg, 0.14 mmol) and PdCl$_2$(dppf)DCM (4 mg). The resulting mixture was stirred at 80° C. for 15 hours under N$_2$. After cooled to room temperature, the mixture was filtered and the filtrate was concentrated under reduced pressure. The residue was purified by prep-TLC and prep-HPLC to give Example 17 (5.4 mg) as a white solid. $^1$H NMR (400 MHz, MeOD) δ 8.29 (s, 1H), 8.03 (dt, J=2.5, 8.0 Hz, 1H), 7.78 (s, 1H), 7.43 (dd, J=6.4, 9.9 Hz, 2H), 7.11 (dd, J=2.4, 8.6 Hz, 1H), 4.43-4.31 (m, 1H), 4.18 (dt, J=5.1, 11.8 Hz, 1H), 3.24-3.18 (m, 2H), 3.01-2.88 (m, 1H), 2.47-2.23 (m, 2H). MS obsd (ESI) [(M+H)$^+$]: 391.

Example 18

3-[4-(5-methyl-1,2,4-oxadiazol-3-yl)-2-oxo-pyrrolidin-1-yl]-N-(3,4,5-trifluorophenyl)-4,5,6,7-tetrahydropyrazolo[1,5-a]pyridine-5-carboxamide

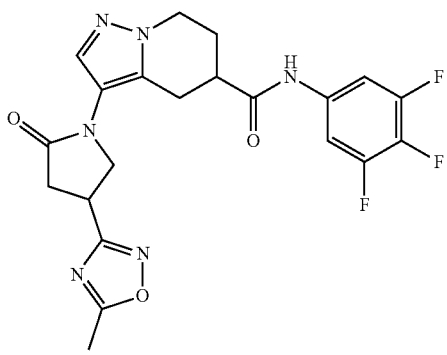 [SMILES: Cc1nc(C2CC(=O)N(c3cnn4c3CC(C(=O)Nc3cc(F)c(F)c(F)c3)CC4)C2)no1]

The title compound was prepared according to the following scheme:

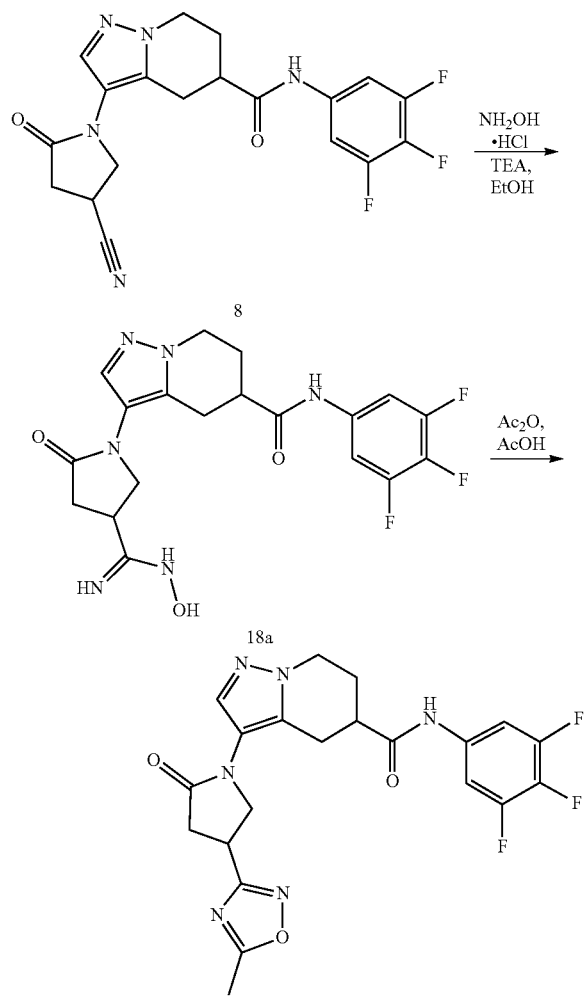

Step 1: Preparation of 3-[4-(N-hydroxycarbamimidoyl)-2-oxo-pyrrolidin-1-yl]-N-(3,4,5-trifluorophenyl)-4,5,6,7-tetrahydropyrazolo[1,5-a]pyridine-5-carboxamide (Compound 18a)

To a solution of 3-(4-cyano-2-oxo-pyrrolidin-1-yl)-N-(3,4,5-trifluorophenyl)-4,5,6,7-tetrahydropyrazolo[1,5-a]pyridine-5-carboxamide (Example 8, 10 mg, 0.02 mmol) in EtOH (0.1 mL) was added hydroxylamine hydrochloride (1.6 mg, 0.05 mmol) and TEA (0.01 mL, 0.07 mmol). The resulting mixture was stirred at 80° C. for 15 hours, then cooled down and concentrated under reduced pressure to give crude compound 18a (12 mg) as a yellow oil. MS obsd (ESI) [(M+H)$^+$]: 437.

Step 2: Preparation of

To a mixture of 3-[4-(N-hydroxycarbamimidoyl)-2-oxo-pyrrolidin-1-yl]-N-(3,4,5-trifluorophenyl)-4,5,6,7-tetrahydropyrazolo[1,5-a]pyridine-5-carboxamide (compound 18a, 12 mg, crude) in AcOH (0.2 mm) was added Ac$_2$O (28 mg, 0.27 mmol). The resulting mixture was stirred at 80° C. for 15 hours, then cooled down to room temperature and filtered. The filtrate was concentrated under reduced pressure. The residue was purified by prep-HPLC to give Example 18 (2.8 mg) as a white solid. $^1$H NMR (400 MHz, MeOD) δ 8.52 (s, 1H), 7.57-7.52 (m, 1H), 7.48-7.40 (m, 2H), 4.34-4.26 (m, 1H), 4.24-4.04 (m, 2H), 4.02-3.87 (m, 2H), 3.10-2.87 (m, 4H), 2.86-2.73 (m, 1H), 2.58 (d, 3H), 2.42-2.31 (m, 1H), 2.30-2.20 (m, 1H). MS obsd (ESI) [(M+H)$^+$]: 461.

Example 19: HBV Inhibition Assays

Cell Line and Culture Conditions:

HepG2.2.15 is a stably-transfected cell line containing the HBV genome. It is derived from the hepatoblastoma cell line Hep G2 (American Type Culture Collection, ATCC® HB-8065™) by the published procedures described in reference: MA Selles et al. Proc. Natl. Acad. Sci. USA 1987, 84, 1005-1009. The cell line was maintained in Dulbecco's modified Eagle's medium and nutrient mixture F-12 (DMEM/F-12, Gibco, Cat. #: 11320-033) supplemented with 10% fetal bovine serum (Gibco, Cat. #: 10099-141), 100 U/mL penicillin, 100 µg/mL streptomycin (Gibco, Cat. #: 15140-122), and 0.3 mg/mL of G418 Sulfate (Gibco, Cat. #: 10131-027).

Anti-HBV Activity In Vitro:

HepG2.2.15 cells were seeded into 96-well plates at a density of 3×10$^4$ cells per well in culture media of 100 µL DMEM/F-12 supplemented with 2.5% fetal bovine serum, 100 U/mL penicillin, 100 µg/mL streptomycin and cultured overnight at 37° C. The test compounds were serially half-log diluted in DMSO, then diluted 100 times in culture media. 100 µL culture media containing diluted compounds were added into the plates to reach 0.5% final concentration of DMSO in every well. Five days after compound treatment, culture supernatant was collected for further analysis.

For quantitative PCR detection of extracellular HBV DNA, culture supernatant was processed by 500 µg/mL Proteinase K (Sigma, Cat. #: P2308) digestion at 50° C. for 1 hour. After heat inactivation of the enzyme at 95° C. for 15 minutes, the samples were subjected to HBV DNA quantification by qPCR. The effective compound concentration at which HBV replication was inhibited by 50% (EC$_{50}$) was determined.

The Examples of the present invention were tested in the above assays as described herein and found to have $EC_{50}$ less than 1 μM in HepG2.2.15 assay as shown in Table 1 below.

TABLE 1

Activity of compounds of this invention in HepG2.2.15 assay

| Example No | $EC_{50}$ (μM) |
|---|---|
| 1 | 0.37 |
| 2 | 0.30 |
| 3 | 0.16 |
| 4 | 0.15 |
| 5 | 0.039 |
| 6 | 0.24 |
| 7 | 0.11 |
| 8 | 0.19 |
| 9 | 0.84 |
| 10 | 0.33 |
| 11 | 0.59 |
| 12 | 0.87 |
| 13 | 0.21 |
| 14 | 0.089 |
| 15 | 0.45 |
| 16 | 0.35 |
| 18 | 0.39 |

The invention claimed is:

1. A compound of formula (I),

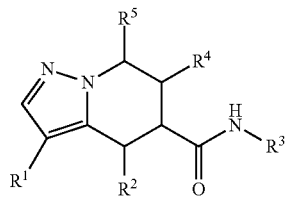

wherein:
$R^1$ is $C_{3-7}$cycloalkyl;
dioxothiadiazolidinyl, said dioxothiadiazolidinyl being unsubstituted or substituted by benzyl;
dioxothiazolidinyl;
oxomorpholinyl;
oxooxazolidinyl, said oxooxazolidinyl being once or twice substituted by $C_{1-6}$alkyl;
oxopyrrolidinyl, said oxooxazolidinyl being unsubstituted or substituted by cyano or $C_{1-6}$alkyloxadiazolyl;
phenyl, said phenyl being once or twice substituted by halogen; or
pyridinyl, said pyridinyl being once or twice substituted by halogen;
$R^2$ is H or $C_{1-6}$alkyl;
$R^3$ is phenyl, said phenyl being once, twice or three times substituted by substituents independently selected from cyano, halogen, $C_{1-6}$alkyl and halo$C_{1-6}$alkyl;
pyridinyl, said pyridinyl being once or twice substituted by halogen; or
thienyl;
$R^4$ is H or $C_{1-6}$alkyl; and
$R^5$ is H or $C_{1-6}$alkyl;
or a pharmaceutically acceptable salt, enantiomer or diastereomer thereof.

2. A compound according to claim 1, wherein:
$R^1$ is $C_{3-7}$cycloalkyl;
dioxothiadiazolidinyl, said dioxothiadiazolidinyl being unsubstituted or substituted by benzyl;
dioxothiazolidinyl;
oxomorpholinyl;
oxooxazolidinyl, said oxooxazolidinyl being twice substituted by $C_{1-6}$alkyl;
oxopyrrolidinyl, said oxooxazolidinyl being unsubstituted or substituted by cyano or $C_{1-6}$alkyloxadiazolyl;
phenyl, said phenyl being twice substituted by halogen; or
pyridinyl substituted by halogen;
$R^2$ is H;
$R^3$ is phenyl, said phenyl being once, twice or three times substituted by substituents independently selected from cyano, halogen, $C_{1-6}$alkyl and halo$C_{1-6}$alkyl;
pyridinyl, said pyridinyl being once or twice substituted by halogen; or
thienyl;
$R^4$ is H; and
$R^5$ is H;
or a pharmaceutically acceptable salt, enantiomer or diastereomer thereof.

3. A compound according to claim 2, wherein:
$R^1$ is cyclopentyl, dioxothiadiazolidinyl, benzyldioxothiadiazolidinyl, dioxothiazolidinyl, oxomorpholinyl, dimethyloxooxazolidinyl, oxopyrrolidinyl, cyanooxopyrrolidinyl, methyloxadiazolyloxopyrrolidinyl, difluorophenyl or fluoropyridinyl;
$R^2$ is H;
$R^3$ is cyanofluorophenyl, methylfluorophenyl, trifluorophenyl, trifluoromethylfluorophenyl, fluoropyridinyl, difluoropyridinyl or thienyl;
$R^4$ is H; and
$R^5$ is H;
or a pharmaceutically acceptable salt, enantiomer or diastereomer thereof.

4. A compound selected from:
3-(2-oxopyrrolidin-1-yl)-N-(3,4,5-trifluorophenyl)-4,5,6,7-tetrahydropyrazolo[1,5-a]pyridine-5-carboxamide;
3-(5,5-dimethyl-2-oxo-oxazolidin-3-yl)-N-(3,4,5-trifluorophenyl)-4,5,6,7-tetrahydropyrazolo[1,5-a]pyridine-5-carboxamide;
3-(2,4-difluorophenyl)-N-(3,4,5-trifluorophenyl)-4,5,6,7-tetrahydropyrazolo[1,5-a]pyridine-5-carboxamide;
3-cyclopentyl-N-(3,4,5-trifluorophenyl)-4,5,6,7-tetrahydropyrazolo[1,5-a]pyridine-5-carboxamide;
3-(1,1-dioxo-1,2-thiazolidin-2-yl)-N-(3,4,5-trifluorophenyl)-4,5,6,7-tetrahydropyrazolo[1,5-a]pyridine-5-carboxamide;
3-(5-benzyl-1,1-dioxo-1,2,5-thiadiazolidin-2-yl)-N-(3,4,5-trifluorophenyl)-4,5,6,7-tetrahydropyrazolo[1,5-a]pyridine-5-carboxamide;
3-(1,1-dioxo-1,2,5-thiadiazolidin-2-yl)-N-(3,4,5-trifluorophenyl)-4,5,6,7-tetrahydropyrazolo[1,5-a]pyridine-5-carboxamide;
3-(4-cyano-2-oxo-pyrrolidin-1-yl)-N-(3,4,5-trifluorophenyl)-4,5,6,7-tetrahydropyrazolo[1,5-a]pyridine-5-carboxamide;
3-(3-oxomorpholin-4-yl)-N-(3,4,5-trifluorophenyl)-4,5,6,7-tetrahydropyrazolo[1,5-a]pyridine-5-carboxamide;
3-[4-(3-methyl-1,2,4-oxadiazol-5-yl)-2-oxo-pyrrolidin-1-yl]-N-(3,4,5-trifluorophenyl)-4,5,6,7-tetrahydropyrazolo[1,5-a]pyridine-5-carboxamide;
3-(2,4-difluorophenyl)-N-(3-thienyl)-4,5,6,7-tetrahydropyrazolo[1,5-a]pyridine-5-carboxamide;
3-(2,4-difluorophenyl)-N-[4-fluoro-3-(trifluoromethyl)phenyl]-4,5,6,7-tetrahydropyrazolo[1,5-a]pyridine-5-carboxamide;

N-(3-cyano-4-fluoro-phenyl)-3-(2,4-difluorophenyl)-4,5,6,7-tetrahydropyrazolo[1,5-a]pyridine-5-carboxamide;
3-(2,4-difluorophenyl)-N-(4-fluoro-3-methyl-phenyl)-4,5,6,7-tetrahydropyrazolo[1,5-a]pyridine-5-carboxamide;
3-(2,4-difluorophenyl)-N-(2,6-difluoro-4-pyridyl)-4,5,6,7-tetrahydropyrazolo[1,5-a]pyridine-5-carboxamide;
3-(2,4-difluorophenyl)-N-(2-fluoro-4-pyridyl)-4,5,6,7-tetrahydropyrazolo[1,5-a]pyridine-5-carboxamide;
3-(6-fluoro-3-pyridyl)-N-(3,4,5-trifluorophenyl)-4,5,6,7-tetrahydropyrazolo[1,5-a]pyridine-5-carboxamide; and
3-[4-(5-methyl-1,2,4-oxadiazol-3-yl)-2-oxo-pyrrolidin-1-yl]-N-(3,4,5-trifluorophenyl)-4,5,6,7-tetrahydropyrazolo[1,5-a]pyridine-5-carboxamide.

5. A method for preparing a compound of formula Ia, the method comprising:
reacting iodide (IV)

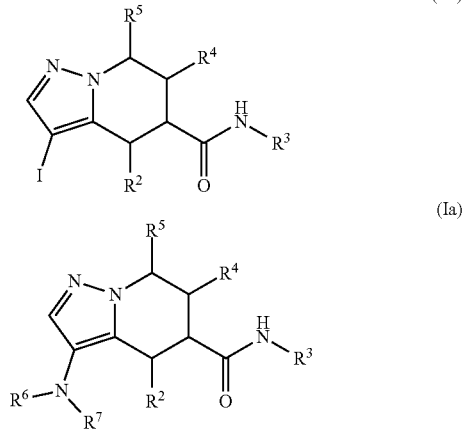

with an amine of formula $R^6R^7NH$ in the presence of a copper catalyst to form compound Ia, wherein:
$R^2$ is H or $C_{1-6}$alkyl
$R^3$ is phenyl, said phenyl being once, twice or three times substituted by substituents independently selected from cyano, halogen, $C_{1-6}$alkyl and halo$C_{1-6}$alkyl;
pyridinyl, said pyridinyl being once or twice substituted by halogen; or
thienyl;
$R^4$ is H or $C_{1-6}$alkyl;
$R^5$ is H or $C_{1-6}$alkyl; and
$R^6$ and $R^7$ together with the nitrogen atom to which they are attached form a 3-7 membered heterocyclyl group.

6. A pharmaceutical composition comprising a compound in accordance with claim 1, or a pharmaceutically acceptable salt, enantiomer or diastereomer thereof, and a therapeutically inert carrier.

7. A method for treating hepatitis B virus infection, which method comprises administering a therapeutically effective amount of a compound as defined in claim 1 to a patient in need thereof.

8. A pharmaceutical composition comprising a compound according to claim 4, or a pharmaceutically acceptable salt, enantiomer or diastereomer thereof, together with a pharmaceutically acceptable carrier or excipient.

9. A method for treating hepatitis B virus infection, which method comprises administering a therapeutically effective amount of a compound as defined in claim 4 to a patient in need thereof.

10. The method of claim 5, wherein the copper catalyst is CuI.

11. The method of claim 5, wherein $R^6$ and $R^7$ together with the nitrogen atom to which they are attached form a heterocyclyl group selected from: dioxothiadiazolidinyl, dioxothiazolidinyl, oxomorpholinyl, oxooxazolidinyl, and oxopyrrolidinyl.

12. The method of claim 5, wherein compound IV is formed by:

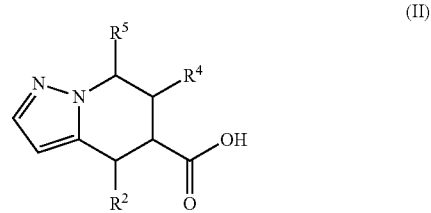

reacting acid (II) with an amine of formula $R^3NH_2$ in the presence of a coupling reagent and a base to give amide (III);

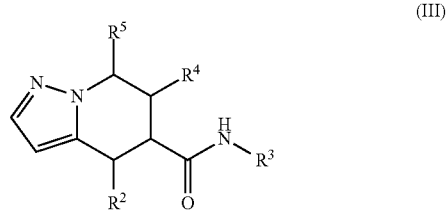

and
treating (III) with an iodinating agent to give iodide (IV).

13. A method for preparing a compound of formula Ib, the method comprising:
reacting iodide (IV),

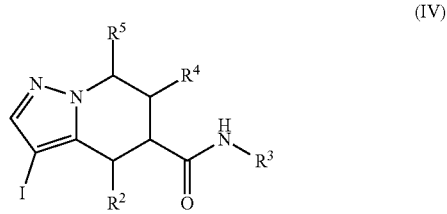

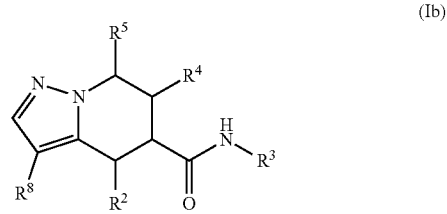

with a boronic acid of formula $R^8$—$B(OH)_2$ in the presence of a palladium catalyst to form compound Ib, wherein:
$R^2$ is H or $C_{1-6}$alkyl;
$R^3$ is phenyl, said phenyl being once, twice or three times substituted by substituents independently selected from cyano, halogen, $C_{1-6}$alkyl and halo$C_{1-6}$alkyl;

pyridinyl, said pyridinyl being once or twice substituted by halogen; or thienyl;

$R^4$ is H or $C_{1-6}$alkyl;

$R^5$ is H or $C_{1-6}$alkyl; and $R^8$ is aryl, heteroaryl or $C_{3-7}$cycloalkyl.

14. The method of claim 13, wherein the palladium catalyst is $PdCl_2(dppf)$.

15. The method of claim 13, wherein compound IV is formed by:

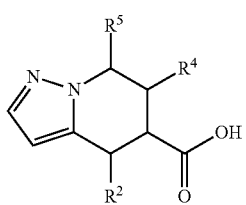
(II)

reacting acid (II) with an amine of formula $R^3NH_2$ in the presence of a coupling reagent and a base to give amide (III);

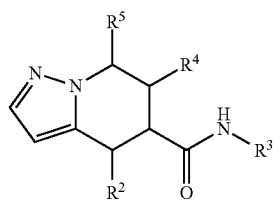
(III)

and treating (III) with an iodinating agent to give iodide (IV).

16. A method for preparing a compound of formula Ib, the method comprising:

reacting a compound of formula (VI)

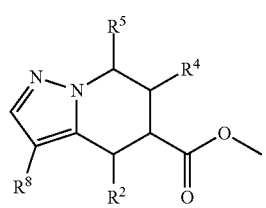
(VI)

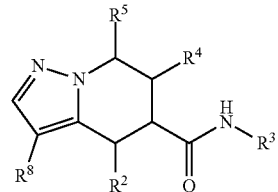
(Ib)

with a first base to form an acid, followed by:

coupling the acid with an amine of formula $R^3NH_2$ in the presence of a coupling reagent and a second base to form compound Ib; or converting the acid to an acyl chloride before reacting with an amine of formula $R^3NH_2$, wherein:

$R^2$ is H or $C_{1-6}$alkyl;

$R^3$ is phenyl, said phenyl being once, twice or three times substituted by substituents independently selected from cyano, halogen, $C_{1-6}$alkyl and halo$C_{1-6}$alkyl;

pyridinyl, said pyridinyl being once or twice substituted by halogen; or thienyl;

$R^4$ is H or $C_{1-6}$alkyl;

$R^5$ is H or $C_{1-6}$alkyl; and $R^8$ is aryl, heteroaryl or $C_{3-7}$cycloalkyl.

17. The method of claim 16, wherein compound VI is formed by:

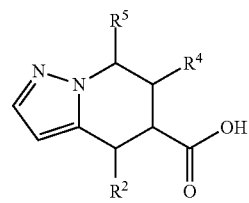
(II)

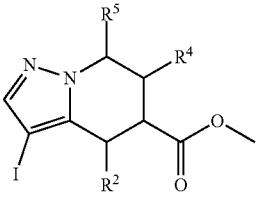
(V)

esterification of compound (II), followed by iodination, to give compound (V);

and reacting (V) with a boronic acid of formula $R^8$—$B(OH)_2$ in the presence of a palladium catalyst to form compound (VI).

* * * * *